United States Patent [19]

Ishiguro et al.

[11] Patent Number: 5,563,137
[45] Date of Patent: Oct. 8, 1996

[54] HEXAHYDROPYRANO [3,2-B] [1,4] BENZOTHIAZINE DERIVATIVE

[75] Inventors: Susumu Ishiguro, Omiya; Shinichi Shimada, Utsunomiya; Motohide Seya, Tochigi-ken; Yuzo Yagi, Utsunomiya; Naomi Kito; Noboru Kawaguchi, both of Tochigi-ken; Masamichi Nakakoshi, Utsunomiya; Kunio Tomitsuka, Kazo; Shin Nomoto; Masayuki Okue, both of Tochigi-ken; Nobuo Ogane, Utsunomiya; Yasunari Saito, Koyama, all of Japan

[73] Assignee: Snow Brand Milk Products Co., Ltd., Hokkaido, Japan

[21] Appl. No.: 400,585

[22] Filed: Mar. 8, 1995

[30] Foreign Application Priority Data

Mar. 9, 1994 [JP] Japan ................. 6-064420

[51] Int. Cl.$^6$ .............. C07D 513/04; A61K 31/54
[52] U.S. Cl. ............. 514/224.5; 514/63; 544/32
[58] Field of Search ............ 544/32; 514/63, 514/224.5

[56] References Cited

FOREIGN PATENT DOCUMENTS 1116525  6/1968  United Kingdom ............ 544/32

Primary Examiner—John M. Ford
Attorney, Agent, or Firm—Browdy and Neimark

[57] ABSTRACT

Particular hexahydropyrano [3,2-b] [1,4] benzothiazine derivatives represented by the following general formula (I) or pharmaceutically acceptable acid-addition salts thereof.

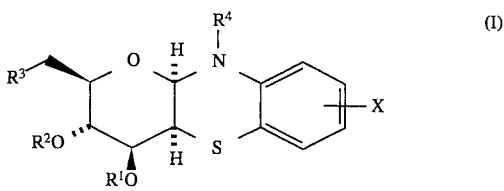

The compounds can facilitate the metabolic turnover of inositol phospholipids at a hippocampus playing an important part in memory, and improve cerebral function leading the memory. The compounds can be utilized as agents for activating brain metabolism and improving cerebral function.

10 Claims, No Drawings

HEXAHYDROPYRANO [3,2-B] [1,4] BENZOTHIAZINE DERIVATIVE

BACKGROUND OF THE INVENTION

1. Field of the Invention

The present invention relates to new hexahydropyrano [3, 2-b] [1, 4] benzothiazine derivatives and pharmaceutically acceptable acid-addition salts thereof. Further, the present invention relates to agents for activating brain metabolism and improving cerebral function comprising an effective amount of a hexahydropyrano [3, 2-b] 1, 4] benzothiazine derivative or a pharmaceutically acceptable acid-addition salt thereof.

2. Description of the Prior Art

Patients suffering from senile dementia increase in number every year to become a social problem. The clinical symptoms of senile dementia comprise the nucleus of symptoms such as defects of memory, disorientation, understanding and judgment troubles and attendant mental symptoms such as depression, night delirium, delusion and hallucination, and emotional indifference. Although conventional agents for activating brain metabolism and for improving cerebral function are effective on improvement of attendant mental symptoms of senile dementia, these agents are not effective on improvement of nucleus symptoms. According to the study of a synapse level of memory, it suggests that a calcium signal and protein kinase C play an important role in the bases of processes of memory [Lynch and Baudry, Science, vol. 224, pp. 1057–1063 (1984); Akers et al., Science, vol. 231, pp. 587–589 (1986); Alkon, Scientific American, vol. 261, pp. 42–50 (1989); Olds et al., Science, vol. 245, pp. 866–869 (1989)]. It becomes clear that release of calcium and activation of protein kinase C are caused by inositol 1,4, 5-trisphosphate, which are produced by hydrolysis of phosphatidyl inositol 4, 5-diphosphate of an inositol phospholipid, and diacylglycerol. [Berridge and Irvine, Nature, vol. 312, pp. 315–321 (1984); Nishizuka, Science, vol. 233, pp. 305–312 (1986)]. Accordingly, materials for facilitating metabolic turnover of the inositol phospholipid of a hippocampus associated with memory are expected as a medicine for improving a deficit of cerebral function, which is nucleus symptoms of dementia, and it is desired to develop such chemicals.

SUMMARY OF THE INVENTION

The present invention aims to provide compounds for facilitating the metabolic turnover of inositol phospholipid at the hippocampus playing an important part in memory to improve the mental function leading the memory, and it also aims to provide agents for activating brain metabolism and improving cerebral function.

Considering the above problems, the inventors of the present invention earnestly have studied and found compounds having an excellent activity against the metabolic turnover of inositol phospholipid at slice samples of a rat hippocampus to complete the present invention. The present invention provides new hexahydropyrano [3, 2-b] [1, 4] benzothiazine derivatives and pharmaceutically acceptable acid-addition salts thereof.

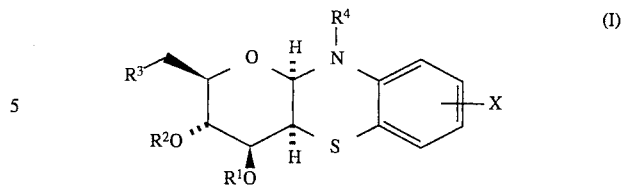

wherein $R^1$ and $R^2$ identical or different, each represents hydrogen, a lower acyl, arylcarbonyl or lower alkoxyalkyl group, or $-SiR^8R^9R^{10}$, or form together a crosslinked disiloxanediyl group having one to four lower alkyl groups, or $R^2$ forms together with $R^5$ a crosslinked disiloxanediyl group having one to four lower alkyl groups, $R^3$ represents an azide group or $YR^5$, $R^4$ represents a lower alkyl, aralkyl or arylcarbonyl group or $-A-NR^6R^7$, X represents hydrogen or halogen, $R^5$ represents hydrogen, a lower alkyl, lower acyl, aryl, arylcarbonyl, lower alkylsulfonyl or arylsulfonyl group or $-SiR^8R^9R^{10}$ or $(CH_2)_n$ $CR^{11}R^{12}R^{13}$ or forms together with $R^2$ a crosslinked disiloxanediyl group having one to four lower alkyl groups, $R^6$ and $R^7$ identical or different, each represents hydrogen or a lower alkyl group, $R^8$, $R^9$ and $R^{10}$ identical or different, each represents a lower alkyl or aryl group, Y represents oxygen, sulfur or $-NR^{14}$, $R^{14}$ represents hydrogen or an aralkyl group, A represents a lower alkylene group, n represents 0, 1 or 2, $R^{11}$, $R^{12}$ and $R^{13}$ identical or different, each represents hydrogen or an aryl group, said aryl group may have 1 to 3 halogens or lower alkoxy groups on the ring, or two or more said aryl groups may be crosslinked with a lower alkylene group, and the above lower means 1 to 6 straight or branched carbon chains.

In the following, $R^1$–$R^{14}$, A, X, Y and n have the same meaning defined as before, excluding special mention.

The synthesis of the compounds of the present invention can be attained by many methods. The following synthetic methods and descriptions are intended to further illustrate an example and not to limit the invention even though the compounds of the present invention are synthesized by another method.

Reaction formula I

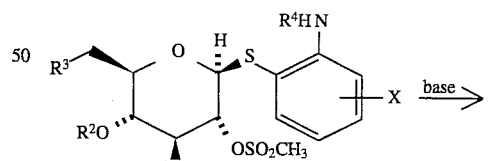

(II)

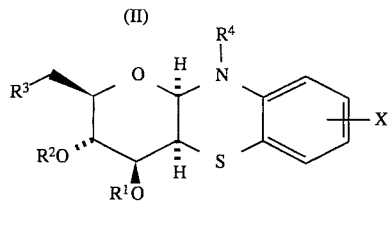

(I)

As shown in Reaction formula I, the compound of general formula (I) is obtained by ring closure reaction of the compound of general formula (II) in an organic solvent in the presence of a base. The solvent used in the reaction is not limited as long as it does not inhibit the reaction, and examples of such solvent include methanol, ethanol, 2-propanol, butanol, dimethylformamide, chloroform, dichloromethane, carbon tetrachloride, diethyl ether, dioxane, tetrahydrofuran, acetonitrile, ethyl acetate, dimethyl sulfoxide and water. In addition, these solvents may be mixed to use in the reaction. Examples of the above base include potassium carbonates, sodium carbonate, potassium bicarbonate, sodium bicarbonate, potassium acetate, sodium acetate, triethylamine, diisopropylethylamine, sodium hydride, calcium hydride and n-butyllithium.

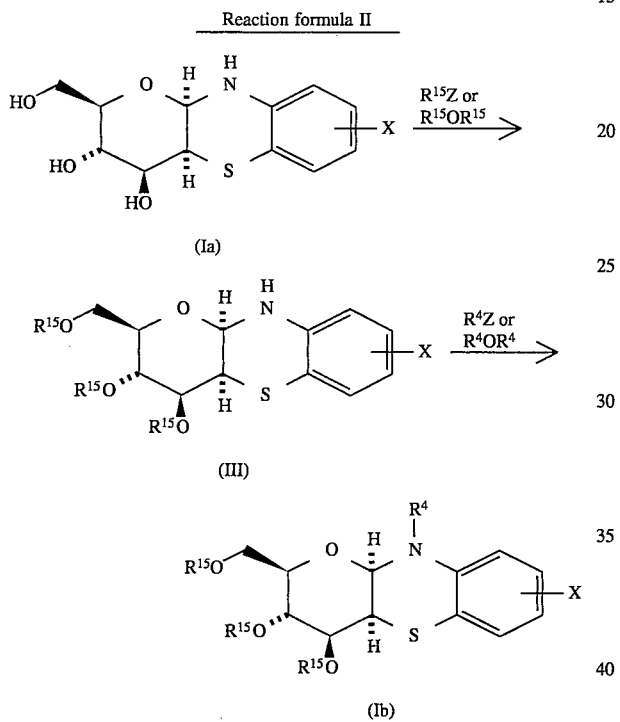

As shown in Reaction formula II, the compound of general formula (Ia) obtained by the same method as in Reaction formula I is treated in the presence of a base with $R^{15}Z$ (wherein $R^{15}$ represents, for example, a lower acyl group, an arylcarbonyl group or $SiR^8R^9R^{10}$, and Z represents halogen), or $R^{15}OR^{15}$ (wherein $R^{15}$ represents, for example, a lower acyl group or an arylcarbonyl group) to obtain the compound of general formula (III). Then, the compound obtained is treated with $R^4Z$ (wherein $R^4$ represents, for example, a lower alkyl group, an aralkyl group, an arylcarbonyl group or —$ANR^6R^7$, and Z represents halogen), or $R^4OR^4$ (wherein $R^4$ represents, for example, a lower acyl group or an arylcarbonyl group) to obtain the compound of general formula (Ib). The solvent used in the above reaction is not limited as long as it does not inhibit the reaction, and examples of such a solvent include dimethylformamide, chloroform, dichloromethane, carbon tetrachloride, diethyl ether, dioxane, tetrahydrofuran, acetonitrile, ethyl acetate, pyridine and dimethyl sulfoxide. In addition, these solvents may be mixed to use in the reaction. Examples of the above base include ammonia, diethylamine, triethylamine, diisopropyl ethylamine, sodium hydride, calcium hydride and n-butyl lithium.

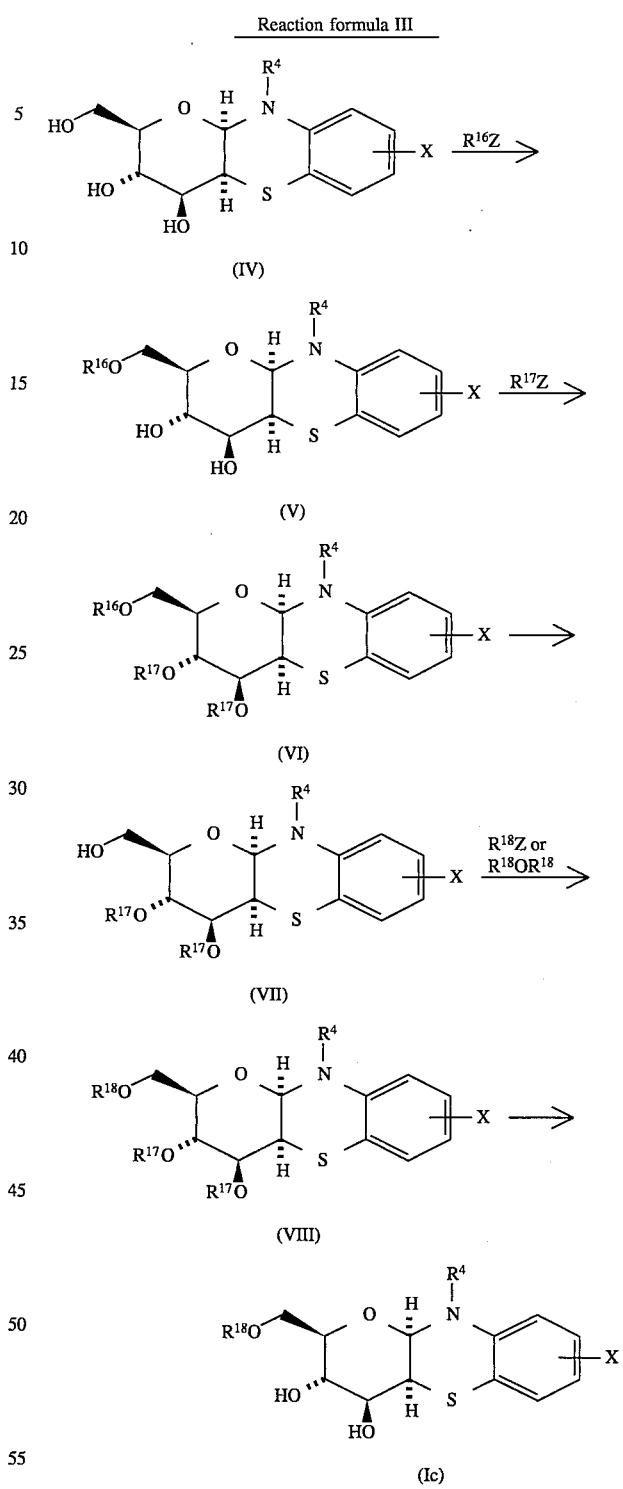

As shown in Reaction formula III, the compound of general formula (IV) is treated with $R^{16}Z$ (wherein $R^{16}$ represents, for example, a typical protection group for a primary hydroxy group, such as —$SiR^8R^9R^{10}$ or —$(CH_2)_nCR^{11}R^{12}R^{13}$ and Z represents halogen) to obtain the compound of general formula (V). The reaction can be performed in any solvent such as pyridine, dimethylformamide, dimethylsulfoxide, methylene chloride, chloroform, carbon tetrachloride, diethyl ether, dioxane, tetrahydrofuran, acetonitrile and ethyl acetate, and mixed solvents thereof as long as it is not inhibited by these solvents. Treating the compound (V) with $R^{17}Z$ (wherein $R^{17}$ represents, for example, a general hydroxyl-protecting group such as a lower acyl group, an arylcarbonyl group, a lower alkoxy alkyl group or $-SiR^8R^9R^{10}$ and Z represents halogen), the compound of general formula (VI) is obtained. After $R^{16}$ is deprotected to obtain the compound of general formula (VII). The compound (VII) is treated with $R^{18}Z$ (wherein $R^{18}$ represents, for example, a lower alkyl group, lower acyl group, an arylcarbonyl group, a lower alkylsulfonyl group, an arylsulfonyl group, $-SiR^8R^9R^{10}$ or $-(CH_2)_nCR^{11}R^{12}R^{13}$, and Z represents halogen) or $R^{18}OR^{18}$ (wherein $R^{18}$ represents, for example, a lower acyl group or an arylcarbonyl group) under basic conditions to obtain the compound of general formula (VIII).

In the reaction, examples of the base used contain ammonia, diethylamine, triethylamine, diisopropyl ethylamine, pyridine, potassium carbonate, sodium carbonate, potassium bicarbonate, sodium bicarbonate, potassium acetate, sodium acetate, sodium methylate and sodium ethylate. The reaction can be performed in any solvent such as dimethylformamide, dimethylsulfoxide, methylene chloride, chloroform, carbon tetrachloride, diethyl ether, dioxane, tetrahydrofuran, acetonitrile and ethyl acetate, and mixed solvents thereof as long as the reaction is not inhibited by these solvents. According as a conventional method, $R^{17}$ is deprotected to obtain the compound of general formula (Ic). Reaction formula IV

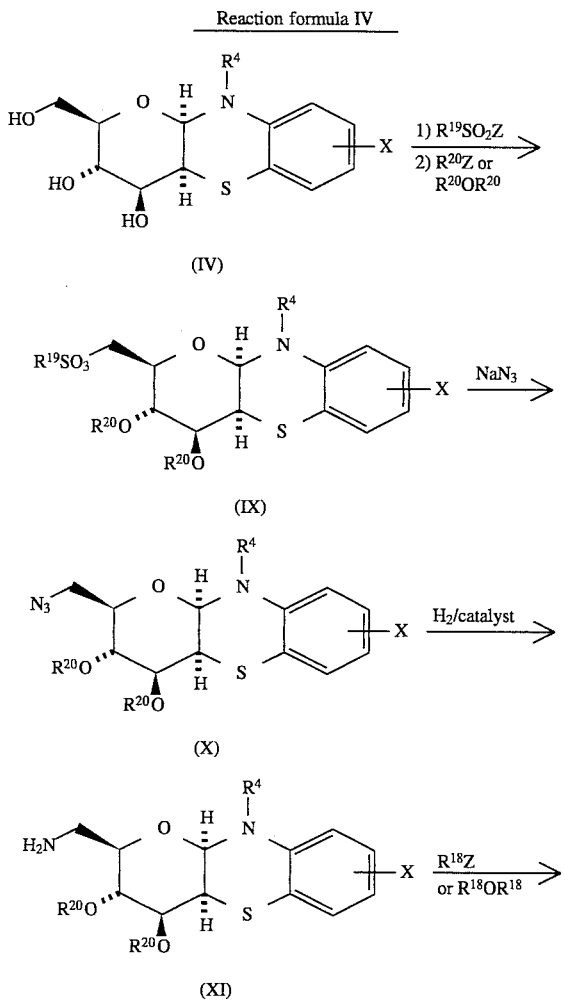

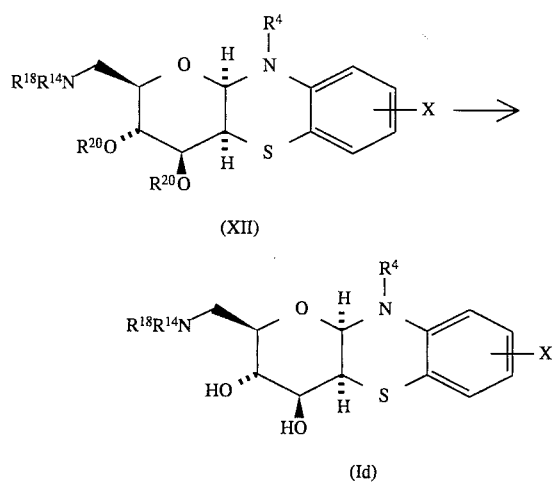

As shown in Reaction formula IV, the compound of general formula (IV) is treated with $R^{19}SO_2^Z$ (wherein $R^{19}$ represents, for example, a lower alkyl or aryl group such as methyl, ethyl, phenyl or tolyl, and Z represents hydrogen or halogen), and then with $R^{20}Z$ (wherein $R^{20}$ represents, for example, a lower acyl group, an arylcarbonyl group, a lower alkoxyalkyl group or $-SiR^8R^9R^{10}$ and Z represents halogen) or $R^{20}OR^{20}$ (wherein $R^{20}$ represents, for example, a lower acyl group or an arylcarbonyl group) to obtain the compound of general formula (IX). The compound is treated with $NaN_3$ to obtain the compound of general formula (X). The reaction can be performed in any solvent such as dimethylformamide, dimethylsulfoxide, methylene chloride, chloroform, carbon tetrachloride, diethyl ether, dioxane, tetrahydrofuran, acetonitrile and ethyl acetate, and mixed solvents thereof as long as the reaction is not inhibited by these solvents. The compound of general formula (XI) is obtained by catalytic reduction of the compound of general formula (X). Examples of the catalyst contain Lindlar, platinum, palladium-carbon and palladium-barium sulfate. The reaction can be performed in any solvent such as methanol, ethanol, water and acetic acid, and mixed solvent thereof as long as the reaction is not inhibited by these solvents. The compound of general formula (XI) is treated with $R^{18}Z$ (wherein $R^{18}$ represents, for example, a lower alkyl group, a lower acyl group, an arylcarbonyl group, a lower alkyl sulfonyl group, an arylsulfonyl group, $-SiR^8R^9R^{10}$ or $-(CH_2)_nCR^{11}R^{12}R^{13}$, and Z represents halogen) or $R^{18}OR^{18}$ (wherein $R^{18}$ represents, for example, a lower acyl group or an arylcarbonyl group) under basic conditions to obtain the compound of general formula (XII). In the reaction, examples of the base used contain ammonia, diethylamine, triethylamine, diisopropyl ethylamine, pyridine, potassium carbonate, sodium carbonate, potassium bicarbonate, sodium bicarbonate, potassium acetate and sodium acetate. The reaction can be performed in any solvent such as dimethylformamide, dimethylsulfoxide, methylene chloride, chloroform, carbon tetrachloride, diethyl ether, dioxane, tetrahydrofuran, acetonitrile and ethyl acetate, and mixed solvents thereof as long as the reaction is not inhibited by these solvents. The compound of general formula (Id) is obtained by deprotection of $R^{20}$ of the compound of general formula (XII) according as conventional procedure.

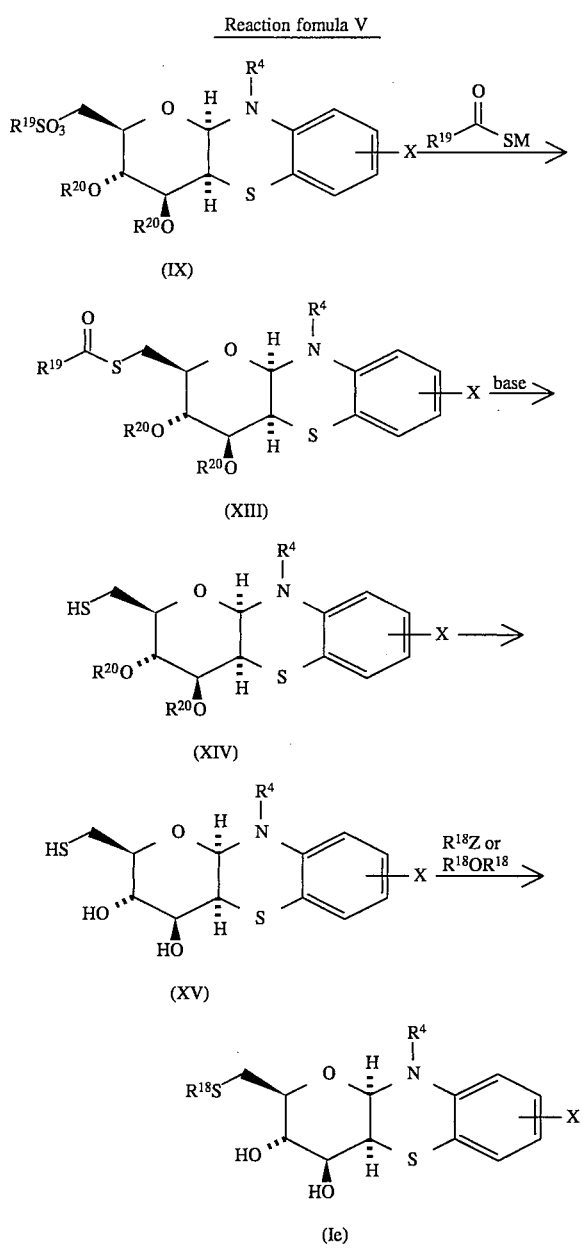

Reaction formula V (IX)

(XIII)

(XIV)

(XV)

(Ie)

As shown in Reaction formula V, the compound of general formula (IX) is treated with $R^{19}C(=O)SM$ (wherein $R^{19}$ represents, for example, a lower alkyl group or an aryl group such as methyl, ethyl, phenyl and tolyl, M represents an alkali metal) to obtain the compound of general formula (XIII). The reaction can be performed in any solvent such as acetone, dimethylformamide, dimethylsulfoxide, methylene chloride, chloroform, carbon tetrachloride, diethyl ether, dioxane, tetrahydrofuran, acetonitrile and ethyl acetate, and mixed solvents thereof as long as it is not inhibited by these solvents. Then, the compound obtained is treated under basic conditions to release mercapto-protecting $R^{19}C(=O)—$, and the compound of general formula (XIV) is obtained. In the reaction, examples of the base used contain ammonia, potassium carbonate, sodium carbonate, potassium bicarbonate, sodium bicarbonate, potassium acetate, sodium acetate, sodium methylate and sodium ethylate. The reaction can be performed in any solvent such as methanol, ethanol, 2-propanol, butanol, water, dimethyl formamide, chloroform, dichloromethane, carbon tetrachloride, diethyl ether, dioxane, tetrahydrofuran, acetonitrile, ethyl acetate and dimethyl sulfoxide, and mixed solvents thereof as long as it is not inhibited by these solution. According as a conventional method, $R^{20}$ is deprotected to obtain the compound of general formula (XV). The compound of general formula (XV) is treated with $R^{18}Z$ (wherein $R^{18}$ represents, for example, a lower alkyl group, a lower acyl group, an arylcarbonyl group, a lower alkyl sulfonyl group, an arylsulfonyl group, $—SiR^8R^9R^{10}$ or $—(CH_2)_nCR^{11}R^{12}R^{13}$ and Z represents halogen) or $R^{18}OR^{18}$ (wherein $R^{18}$ represents, for example, a lower acyl group or an arylcarbonyl group) under basic conditions to obtain the compound of general formula (Ie). In the reaction, examples of the base used contain ammonia, diethylamine, triethylamine, diisopropyl ethylamine, pyridine, potassium carbonate, sodium carbonate, potassium bicarbonate, sodium bicarbonate, potassium acetate, sodium acetate, sodium methylate and sodium ethylate. The reaction can be performed in any solvent such as dimethylformamide, dimethylsulfoxide, methylene chloride, chloroform, carbon tetrachloride, diethyl ether, dioxane, tetrahydrofuran, acetonitrile and ethyl acetate, and mixed solvents thereof as long as it is not inhibited by these solvents.

The compound represented by general formula (III), which is used as a starting material in the above procedure, is prepared in accordance with a method of M. Sekiya and S. Ishiguro et al [Carbohydrate Research, vol, 22, pp. 325–336 (1972)].

The reaction is performed at a temperature of ice cooling to a temperature of refluxing solvent.

Further, the compound (I) of the present invention is separated and purified from the reaction mixture by application of conventional methods such as extraction, concentration, crystallization, filtration, recrystallization or all sorts of chromatography.

The compound (I) of the present invention obtained by using the above methods, if necessary, can be converted to an acid-addition salt. A suitable acid is an inorganic acid such as sulfuric acid, hydrochloric acid, nitric acid, phosphoric acid, hydrobromic acid or carbonic acid, or an organic acid such as acetic acid, lactic acid, succinic acid, tartaric acid, malic acid, citric acid, methane-sulfonic acid, toluenesulfonic acid and benzene-sulfonic acid.

DESCRIPTION OF THE PREFERRED EMBODIMENTS

The following Examples are intended to further illustrate the present invention and not to limit the invention by these Examples.

EXAMPLE 1

(2R, 3R, 4S, 4aS, 10aR)-2-acetoxymethyl-8-chloro-3,4-diacetoxy-10-methyl-2, 3, 4, 4a, 10, 10a-hexahydropyrano [3, 2 -b] [1, 4] benzothiazine (1)

The suspension of 6.00 g of 4'-chloro-2'-methylaminophenyl-3, 4, 6-tri-O-acetyl-2-O-mesyl-1-thio-β-D-glucopyranoside in 80 ml of methanol saturated with hydrogen chloride was stirred at room temperature for two hours. After the reaction solution was concentrated under reduced pressure, 40 ml of ethanol and 40 ml of saturated aqueous sodium bicarbonate were added to the resulting residue, and the mixture was heated under reflux for 20 minutes. After removing the solvent in vacuo, 30 ml of pyridine and 30 ml of acetic anhydride were added to the resulting residue, and the mixture was stirred at room temperature for 20 hours. The reaction solution was poured into ice water, and the precipitate was separated by filtration and washed with water. After air-drying over night, the product was recrystallized from ethanol to obtain 3.70 g (yield: 75.0%) of the title compound.

Melting point: 217°–218° C.
FAB MS: 443 [M+H]$^+$
IR: $\upsilon^{KBr}$cm$^{-1}$: 1750, 1730, 1580, 1490, 1235, 1045
Optical rotation $[\alpha]^{25}_D$ 1.9° (c 5, CHCl$_3$)

| Anal. Calcd. for C$_{19}$H$_{22}$ClNO$_4$S | | | | |
|---|---|---|---|---|
| | C (%) | H (%) | N (%) | S (%) |
| Calcd: | 51.41 | 5.00 | 3.16 | 7.22 |
| Found: | 51.29 | 5.20 | 3.41 | 7.53 |

EXAMPLE 2

(2R, 3S, 4S, 4aS, 10aR)-10-benzyl-8-chloro -3, 4-dihydroxy-2-hydroxymethyl-2, 3, 4, 4a, 10, 10a-hexahydropyrano [3, 2-b] [1, 4] benzothiazine (2)

The solution of 3.50 g of 2'-benzylamino-4'-chlorophenyl- 3, 4, 6-tri-O-acetyl-2-O-mesyl-1-thio-β-D-glucopyranoside in 80 ml of methanol saturated with hydrogen chloride was left at 4° C. for 15 hours. After removing the solvent in vacuo, 40 ml of ethanol and 40 ml of saturated aqueous sodium bicarbonate were added to the resulting residue, and the mixture was heated under reflux for 20 minutes. After removing the solvent in vacuo, the residue was washed with water and recrystallized from 2-propanol to obtain 680 mg (yield: 30.4%) of the title compound.

Melting point: 176°–177° C.
FAB MS: 394 [M+H]$^+$
IR: $\upsilon^{KBr}$cm$^{-1}$: 3450, 1580, 1490, 1045
Optical rotation $[\alpha]^{25}_D$ –56.8° (c 1, CH$_3$OH)

| Anal. Calcd. for C$_{19}$H$_{20}$ClNO$_4$S | | | | |
|---|---|---|---|---|
| | C (%) | H (%) | N (%) | S (%) |
| Calcd: | 57.94 | 5.12 | 3.57 | 8.14 |
| Found: | 57.95 | 5.02 | 3.60 | 7.96 |

EXAMPLE 3

(2R, 3R, 4S, 4aS, 10aR)-2-acetoxymethyl-10-benzyl-8-chloro-3, 4-diacetoxy-2, 3, 4, 4a, I 0, 10a-hexahydropyrano [3, 2-b] [1, 4] benzothiazine (3)

The solution of 460 mg of the compound (2) obtained in Example 2 in a mixed solution of 4 ml of pyridine and 4 ml of acetic anhydride was stirred at room temperature for 20 hours. The reaction mixture was poured into ice water and extracted with chloroform. The organic layer was washed with diluted hydrochloric acid, water, saturated aqueous sodium bicarbonate, and water successively, and dried over anhydrous sodium sulfate, and the solvent was removed under reduced pressure. The resulting residue was crystallized from 2-propanol to obtain 140 mg (yield: 25.2%) of the title compound.

Melting point: 158°–159° C.
FAB MS: 520 [M+H]$^+$
IR: $\upsilon^{KBr}$cm$^{-1}$: 1750, 1580, 1490, 1365, 1220, 1060
Optical rotation $[\alpha]^{25}_D$+14.2° (c 1, CHCl$_3$)

| Anal. Calcd. for C$_{25}$H$_{26}$ClNO$_7$S | | | | |
|---|---|---|---|---|
| | C (%) | H (%) | N (%) | S (%) |
| Calcd: | 57.74 | 5.04 | 2.69 | 6.17 |
| Found: | 57.67 | 5.25 | 2.95 | 5.90 |

EXAMPLE 4

(2R, 3R, 4S, 4aS, 10aR) -2-acetoxymethyl-8-chloro -3, 4-diacetoxy-10-(2-diethylaminoethyl)-2, 3, 4, 4a, 10, 10a-hexahydropyrano [3, 2-b] [1, 4] benzothiazine (4)

According to the method of Example 1, 5.00 g of 4'-chloro-2'-diethylaminoethylaminophenyl-3, 4, 6-tri-O-acetyl-2-O-mesyl-1-thio-β-D-glucopyranoside gave 1.34 g (yield 31.7%) of the title compound.

Melting point: 152° C.
FAB MS: 529 [M+H]$^+$
IR: $\upsilon^{KBr}$cm$^{-1}$: 1740, 1240, 1060, 1040
Optical rotation $[\alpha]^{25}_D$+14.3° (c 1, CHCl$_3$)

| Anal. Calcd. for C$_{24}$H$_{33}$ClN$_2$O$_7$S | | | | |
|---|---|---|---|---|
| | C (%) | H (%) | N (%) | S (%) |
| Calcd: | 54.49 | 6.29 | 5.29 | 6.06 |
| Found: | 54.20 | 6.32 | 5.00 | 6.34 |

EXAMPLE 5

(2R, 3R, 4S, 4aS, 10aR)-2-acetoxymethyl-8-chloro-3, 4-diacetoxy-10-(3-dimethylaminopropyl)-2, 3, 4, 4a, 10, 10a -hexahydropyrano [3, 2-b] [1, 4] benzothiazine (5)

According to the method of Example 1, 12.30 g of 4'-chloro-2'-dimethylaminopropylaminophenyl-3, 4, 6-tri-O-acetyl -2-O-mesyl-1-thio-β-D-glucopyranoside gave 1.86 g (yield 17.9%) of the title compound.

Melting point: 149°–151° C.
FAB MS: 515 [M+H]$^+$
IR: $\upsilon^{KBr}$cm$^{-1}$: 1735, 1240, 1040
Optical rotation $[\alpha]^{25}_D$+2.8° (c 5, CHCl$_3$)

| Anal. Calcd. for C$_{23}$H$_{31}$ClN$_2$O$_7$S | | | | |
|---|---|---|---|---|
| | C (%) | H (%) | N (%) | S (%) |
| Calcd: | 53.64 | 6.07 | 5.44 | 6.23 |
| Found: | 53.34 | 6.08 | 5.47 | 6.30 |

EXAMPLE 6

(2R, 3R, 4S, 4aS, 10aR)-2-acetoxymethyl-8-chloro -3, 4-diacetoxy-10-(2-diethylaminopropyl)-2, 3, 4, 4a, 10, 10a -hexahydropyrano [3, 2-b] [1, 4] benzothiazine (6)

According to the method of Example 1, 7.76 g of 4'-chloro-2'-(2-diethylaminopropyl)phenyl-3, 4, 6-tri-O -acetyl-2O-mesyl-1-thio-β-D-glucopyranoside gave 940 mg (yield 14.3%) of the title compound.

FAB MS: 543 [M+H]$^+$
IR: $\upsilon^{KBr}$cm$^{-1}$: 2980, 2940, 1750, 1585, 1495, 1370, 1230, 1060

EXAMPLE 7

(2R, 3S, 4S, 4aS, 10aR)-8-chloro-3, 4-dihydroxy-2-hydroxymethyl-10-methyl-2, 3, 4, 4a, 10, 10a-hexahydropyrano [3, 2-b] [1, 4] benzothiazine (7)

The suspension of 1.50 g of the compound (1) obtained in Example 1 in 50 ml of methanol saturated with ammonia was allowed to stand at 4° C. for 24 hours. The reaction solution was concentrated under reduced pressure. To the resulting residue water was added, and the precipitated product was filtered and washed with water, and ether successively. The resulting crude product was recrystallized with 2-propanol to obtain 600 mg (yield: 55.9%) of the title compound.

Melting point: 187°–188° C.
FAB MS: 318 [M+H]$^+$
IR: $\upsilon^{KBr}$cm$^{-1}$: 13450, 1580, 1490, 1170
Optical rotation $[\alpha]^{25}_D$ –37.4° (c 1, CH$_3$OH )

| | Anal. Calcd. for C$_{13}$H$_{16}$ClNO$_4$S | | | |
|---|---|---|---|---|
| | C (%) | H (%) | N (%) | S (%) |
| Calcd: | 49.13 | 5.07 | 4.41 | 10.09 |
| Found: | 49.06 | 5.31 | 4.36 | 10.12 |

EXAMPLE 8

(2R, 3S, 4S, 4aS, 10aR)-8-chloro-10-(2-diethylaminoethyl)-3, 4-dihydroxy-2-hydroxymethyl-2, 3, 4, 4a, 10, 10a-a-hexahydropyrano [3, 2-b] [1, 4] benzothiazine (8)

The compound (4) 800 mg obtained in Example 4 was treated in the same manner of Example 7, and 370 mg (yield: 61.4% ) of the title compound was obtained.

Melting point: 134°–137° C.
FAB MS: 403 [M+H]$^+$
IR: $\upsilon^{KBr}$cm$^{-1}$: 3400, 1580, 1060
Optical rotation $[\alpha]^{25}_D$ –31.2° (c 1, CH$_3$OH)

| | Anal. Calcd. for C$_{18}$H$_{27}$ClN$_2$O$_4$S | | | |
|---|---|---|---|---|
| | C (%) | H (%) | N (%) | S (%) |
| Calcd: | 53.66 | 6.75 | 6.95 | 7.96 |
| Found: | 53.56 | 6.75 | 6.97 | 7.71 |

EXAMPLE 9

(2R, 3S, 4S, 4aS, 10aR)-8-chloro-10-(3-dimethylaminopropyl)-3, 4-dihydroxy-2-hydroxymethyl-2, 3, 4, 4a, 10, 10a-a-hexahydropyrano [3, 2-b] [1, 4] benzothiazine (9)

800 mg of the compound (5) obtained in Example 5 was treated in the same manner of Example 7, and 370 mg (yield: 61.4%) of the title compound was obtained.

Melting point: 160°–162° C.
FAB MS: 389 [M+H]$^+$
IR: $\upsilon^{KBr}$cm$^{-1}$: 3380, 1580, 1060
Optical rotation $[\alpha]^{25}_D$ –70.6° (c 1, CH$_3$OH )

| | Anal. Calcd. for C$_{17}$H$_{25}$ClN$_2$O$_4$S | | | |
|---|---|---|---|---|
| | C (%) | H (%) | N (%) | S (%) |
| Calcd: | 52.50 | 6.48 | 7.20 | 8.24 |
| Found: | 52.27 | 6.73 | 7.23 | 8.43 |

EXAMPLE 10

(2R, 3S, 4S, 4aS, 10aR)-8-chloro-10-(2-diethylaminopropyl)-3, 4-dihydroxy-2-hydroxymethyl-2, 3, 4, 4a, 10, 10a-hexahydropyrano [3, 2-b] [1, 4] benzothiazine (10)

The compound (6) 240 mg obtained in Example 6 was treated in the same manner of Example 7, and 60 mg (yield: 32.7%) of the title compound was obtained.

Melting point: 185°–188° C.
FAB MS: 417 [M+H]$^+$
IR: $\upsilon^{KBr}$cm$^{-1}$: 3400, 3300, 2975, 1585, 1490, 1390, 1070

| | Anal. Calcd. for C$_{19}$H$_{29}$ClN$_2$O$_4$S | | | |
|---|---|---|---|---|
| | C (%) | H (%) | N (%) | S (%) |
| Calcd: | 54.73 | 7.01 | 6.72 | 7.69 |
| Found: | 54.46 | 7.13 | 6.52 | 7.25 |

EXAMPLE 11

(2R, 3R, 4S, 4aS, 10aR)-8-chloro-10-(2-diethylaminoethyl)-3, 4-dipropionyloxy-2-propionyloxymethyl-2, 3, 4, 4a, 10, 10a-hexahydropyrano [3, 2-b] [1, 4] benzothiazine (11)

According to the method of Example 3, 2.07 g of the compound (8) obtained in Example 8 was treated with propionic anhydride to give 1.07 g (yield: 36.7%) of the title compound.

Melting point: 125°–127° C.
FAB MS: 571 [M+H]$^+$
IR: $\upsilon^{KBr}$cm$^{-1}$: 2970, 1740, 1580, 1485, 1180, 1080
Optical rotation $[\alpha]^{25}_D$ 13.8° (c 1, CHCl$_3$)

| | Anal. Calcd. for C$_{27}$H$_{39}$ClN$_2$O$_7$S | | | |
|---|---|---|---|---|
| | C (%) | H (%) | N (%) | S (%) |
| Calcd: | 56.78 | 6.88 | 4.90 | 5.61 |
| Found: | 56.73 | 7.05 | 4.88 | 5.65 |

EXAMPLE 12

(2R, 3R, 4S , 4aS, 10aR)-8-chloro-10-(2-diethylamino-ethyl)-2-butyryloxymethyl-3, 4-dibutylyloxy-2, 3, 4, 4a, 10, 10a-hexahydropyrano [3, 2-b] [1, 4] benzothiazine (12)

According to the method of Example 3, 2.07 g of the compound (8) obtained in Example 8 was treated with butyric anhydride to obtain 1.51 g (yield: 48.7%) of the title compound.

Melting point: 92°–94° C.
FAB MS: 613 [M+H]$^+$
IR: $\upsilon^{KBr}$cm$^{-1}$: 2970, 1740, 1730, 1580, 1485, 1180
Optical rotation $[\alpha]^{25}_D$ +14.6° (c 1, CHCl$_3$)

| | Anal. Calcd. for C$_{30}$H$_{45}$ClN$_2$O$_7$S | | | |
|---|---|---|---|---|
| | C (%) | H (%) | N (%) | S (%) |
| Calcd: | 58.76 | 7.40 | 4.57 | 5.23 |
| Found: | 58.72 | 7.65 | 4.68 | 5.00 |

EXAMPLE 13

(2R, 3R, 4S, 4aS, 10aR)-8-chloro-3, 4-dibenzoyloxy-10 -(2-diethylaminoethyl)-2-benzoyloxymethyl-2, 3, 4, 4a, 10, 10a-hexahydropyrano [3, 2-b] [1, 4] benzothiazine (13)

To the solution of 2.04 g of the compound (8) obtained in Example 8 in 30 ml of pyridine, 4 ml of benzoyl chloride was added dropwise at 0° C. The reaction solution was stirred for one hour at 0° C. and then stirred for further one hour at room temperature. The reaction solution was poured into 100 ml of ice water and extracted with chloroform. The organic layer was washed with dilute hydrochloric acid, water, saturated aqueous sodium bicarbonate, and water successively, and then dried over anhydrous sodium sulfate. The solvent was removed under reduced pressure. The resulting residue was crystallized from ethanol to obtain 1.54 g (yield: 42.2%) of the title compound.

Melting point: 124°–126° C.
FAB MS: 715 [M+H]$^+$
IR: $\upsilon^{KBr}$cm$^{-1}$: 2970, 1720, 1580, 1490, 1270, 1110, 710
Optical rotation $[\alpha]^{25}{}_D$+82.2° (c, 1, CHCl$_3$)

| | Anal. Calcd. for C$_{39}$H$_{39}$ClN$_2$O$_7$S | | | |
|---|---|---|---|---|
| | C (%) | H (%) | N (%) | S (%) |
| Calcd: | 65.49 | 5.50 | 3.92 | 4.48 |
| Found: | 65.70 | 5.58 | 3.91 | 4.43 |

EXAMPLE 14

(2R, 3S, 4S, 4aS, 10aR)-2 -tert-butyldimethylsilyloxymethyl-8-chloro-10-(2-diethylaminoethyl)-3,4-dihydroxy -2, 3, 4, 4a, 10, 10a-hexahydropyrano [3, 2-b] [1, 4] benzothiazine (14)

To the solution of 1.03 g of the compound (8) obtained in Example 8 and 0.42 g of imidazole in 2.5 ml of dimethylformamide, 0.47 g of tert-butyldimethylsilyl chloride was added dropwise, and the mixture was stirred for two hours at room temperature. 15 ml of chloroform was added to the reaction solution, and the mixture was washed with saturated aqueous sodium bicarbonate, and water successively. The organic layer was dried over anhydrous magnesium sulfate, and the solvent was removed under reduced pressure. The resulting residue was purified by silica gel column chromatography, and 1.03 g (yield: 80.3%) of the title compound was obtained from the fraction of ethyl acetate-methanol (19:1).

FAB MS: 517 [M+H]$^+$
IR: $\upsilon^{KBr}$cm$^{-1}$: 2950, 2930, 2850, 1580, 1485, 1250, 1060, 835
Optical rotation $[\alpha]^{25}{}_D$–16.7° (c 1, CHCl$_3$)

EXAMPLE 15

(2R, 3R, 4S, 4aS, 10aR)-2 -tert-butyldimethylsilyloxymethyl-8-chloro-3,4-diacetoxy-10-(2-diethylaminoethyl)-2, 3, 4, 4a, 10, 10a-hexahydropyrano [3, 2-b] [1, 4] benzothiazine (15)

The compound (14) 2.20 g obtained in Example 14 was used as the starting material and treated in the same manner of Example 3, and 2.54 g (yield: 99.4%) of the title compound was obtained.

FAB MS: 601 [M+H]$^+$
IR: $\upsilon^{KBr}$cm$^{-1}$: 2970, 2930, 1750, 1580, 1490, 1230, 1050, 830
Optical rotation $[\alpha]^{25}{}_D$+13.8° (c 1, CHCl$_3$)

EXAMPLE 16

(2R, 3R, 4S, 4aS, 10aR)-4-acetoxy-2-acetoxymethyl-8 -chloro-10-(2-diethylaminoethyl)-3-hydroxy-2, 3, 4, 4a, 10, 10a-hexahydropyrano [3, 2-b] [1, 4] benzothiazine (16) and (2R, 3S, 4S, 4aS, 10aR)-3-acetoxy-2 -acetoxymethyl-8-chloro-10-(2-diethylaminoethyl)-4-hydroxy-2, 3, 4, 4a, 10, 10a-hexahydropyrano [3, 2-b] [1, 4] benzothiazine (17)

To the solution of 2.54 g of the compound (15) obtained in Example 15 in 6 ml of tetrahydrofuran, 6 ml of a 1M solution of tetrabutylammoniumfluoride-tetrahydrofuran was added dropwise. The mixture was stirred for one hour at room temperature. Water was added to the reaction solution, and the mixture was extracted with chloroform, the organic layer was dried over anhydrous magnesium sulfate, and the solvent was removed under reduced pressure. The resulting residue was purified by silica gel column chromatography, and 580 mg (yield: 28.3 of the title compound (16) and 510 mg (yield 24.9%) of the title compound (17) were obtained from the fraction of ethyl acetate-hexane (4:1).

The title compound (16)
Melting point: 136°–140° C.
FAB MS: 487 [M+H]$^+$
IR: $\upsilon^{KBr}$cm$^{-1}$: 3450, 2980, 1750, 1585, 1490, 1240, 1070, 1050
Optical rotation $[\alpha]^{25}{}_D$–8.0° (c 3, CHCl$_3$)

| | Anal. Calcd. for C$_{22}$H$_{31}$ClN$_2$O$_6$S | | | |
|---|---|---|---|---|
| | C (%) | H (%) | N (%) | S (%) |
| Calcd: | 54.26 | 6.42 | 5.75 | 6.58 |
| Found: | 53.71 | 6.35 | 5.67 | 7.03 |

The title compound (17)
Melting point: 158°–161 ° C.
FAB MS: 487 [M+H]$^+$
IR: $\upsilon^{KBr}$cm$^{-1}$: 3450, 2980, 1740, 1580, 1485, 1250, 1070
Optical rotation $[\alpha]^{25}{}_D$–15.4° (c 5, CHCl$_3$)

| | Anal. Calcd. for C$_{22}$H$_{31}$ClN$_2$O$_6$S | | | |
|---|---|---|---|---|
| | C (%) | H (%) | N (%) | S (%) |
| Calcd: | 54.26 | 6.42 | 5.75 | 6.58 |
| Found: | 53.79 | 6.67 | 5.80 | 6.96 |

EXAMPLE 17

(6aR, 7aR, 13aS, 14S, 14aR)-10-chloro-8 -(2-diethylaminoethyl)-14-hydroxy-2, 2, 4, 4-tetraisopropyl-6H-6a, 7a, 8, 13a, 14, 14a-hexahydro [1, 3, 5, 2, 4] trioxadisiloxyno [6', 7': 5, 6]pyrano [3, 2-b] [1, 4] benzothiazine (18)

To the solution of 19.28 g of the compound (8) obtained in Example 8 in 25 ml of pyridine, 15 ml of 1, 3-dichloro-1, 1, 3, 3-tetraisopropyldisiloxane was added dropwise. After the mixture was stirred for 30 minutes at room temperature, 0.25 ml of dimethylformamide was added to the reaction solution, and the mixture was stirred for 15 hours at room temperature. The solvent was removed under reduced pressure, and ethyl acetate was added to the resulting residue. The mixture was washed with saturated aqueous sodium bicarbonate, and water successively, and the organic layer was dried over anhydrous magnesium sulfate, and the solvent was removed under reduced pressure. The resulting residue was purified by silica gel column chromatography, and the resulting crystals from the fraction of ethyl acetate-hexane (1:1) were recrystallized with 2-propanol to obtain 10.75 g (yield: 34.8 of the title compound.

Melting point: 147°–148° C.
FAB MS: 645 [M+H]$^+$
IR: $v^{KBr}$cm$^{-1}$: 3450, 2950, 2860, 1580, 1490, 1470, 1100,
Optical rotation [α]$^{25}_D$–36.4° (c 1, CHCl$_3$)

| Anal. Calcd. for C$_{30}$H$_{53}$ClN$_2$O$_5$SSi$_2$ | | | |
|---|---|---|---|
| | C (%) | H (%) | N (%) | S (%) |
| Calcd: | 55.83 | 8.28 | 4.34 | 4.97 |
| Found: | 55.52 | 8.60 | 4.43 | 4.82 |

EXAMPLE 18

(6aR, 7aR, 13aS, 14S, 14aR)-14-acetoxy-10-chloro -8-(2diethylaminoethyl))-2, 2, 4, 4-tetraisopropyl-6H-6a, 7a, 8, 13a, 14, 14a-hexahydro [1, 3, 5, 2, 4] trioxadisiloxyno [6', 7'; 5, 6] pyrano [3, 2-b] [1, 4] benzothiazine (19)

The compound (18) 8.97 g obtained in Example 17 was used as the starting material and treated in the same manner of Example 3, and 6.17 g (yield: 64.7%) of the title compound was obtained.

FAB MS: 687 [M+H]$^+$
IR: $v^{KBr}$cm$^{-1}$: 2950, 2860, 1750, 1580, 1490, 1230, 1100, 1030
Optical rotation [α]$^{25}_D$–30.8° (c 1, CHCl$_3$)

EXAMPLE 19

(2R, 3S, 4S, 4aS, 10aR)-2-acetoxymethyl-8-chloro-10 -(2-diethylaminoethyl)-3, 4-dihydroxy-2, 3, 4, 4a, 10, 10a-hexahydropyrano [3, 2-b] [1, 4] benzothiazine (20)

To the solution of 1.39 g of the compound (19) obtained in Example 18 in 6 ml of tetrahydrofuran, 6 ml of a 1M solution of tetrabutylammoniumfluoride-tetrahydrofuran was added dropwise. The mixture was stirred for one hour at room temperature. The solvent was removed under reduced pressure, water was added to the resulting residue, and the mixture was extracted with chloroform. Combined organic layer was dried over anhydrous magnesium sulfate, and the solvent was removed under reduced pressure. The resulting residue (1.85 g) was purified by silica gel column chromatography, and the resulting crystals from the fraction of ethyl acetate-hexane (4:1) were recrystallized with 2-propanol to obtain 200 mg (yield: 22.3%) of the title compound.

Melting point: 180° C.
FAB MS: 445 [M+H]$^+$
IR: $v^{KBr}$cm$^{-1}$: 3440, 2970, 1715, 1580, 1485, 1275, 1250,
Optical rotation [α]$^{25}_D$–22.4° (c 1, CH$_3$OH

| Anal. Calcd. for C$_{20}$H$_{29}$ClN$_2$O$_5$S | | | |
|---|---|---|---|
| | C (%) | H (%) | N (%) | S (%) |
| Calcd: | 53.98 | 6.57 | 6.30 | 7.21 |
| Found: | 53.49 | 6.81 | 6.22 | 7.11 |

EXAMPLE 20

(2R, 3S, 4S, 4aS, 10aR)-2 -tert-butyldimethylsilyloxymethyl-8-chloro-10-(2-diethylaminopropyl)-3,4-dihydroxy-2, 3, 4, 4a, 10, 10a-hexahydropyrano [3, 2-b] [1, 4] benzothiazine (21)

To the solution of 1.51 g of the compound (10) obtained in Example 10 and 0.48 g of imidazole in 3.5 ml of dimethylformamide, 0.55 g of tert-butyldimethylsilyl chloride was added dropwise, and the mixture was stirred for 23 hours at room temperature. Chloroform was added to the reaction solution, and the mixture was washed with water. The organic layer was dried over anhydrous magnesium sulfate, and the solvent was removed under reduced pressure. The resulting residue was purified by silica gel column chromatography, and 180 mg (yield: 9.4%) of the title compound was obtained from the fraction of ethyl acetate-methanol (19:1).

FAB MS: 531 [M+H]$^+$
IR: $v^{KBr}$cm$^{-1}$: 3450, 2970, 2930, 1585, 1490, 1050, 840

EXAMPLE 21

(2R, 3R, 4S, 4aS, 10aR)-2-acetoxymethyl-10-benzoyl-3, 4 -diacetoxy-2, 3, 4, 4a, 10, 10a-hexahydropyrano [3, 2-b] [1, 4] benzothiazine (22)

To the solution of 5.0 g of (2R, 3R, 4S, 4aS, 10aR)-3, 4-dihydroxy-2-hydroxymethyl-2, 3, 4, 4a, 10, 10 a-hexahydropyrano [3, 2-b] [1, 4] benzothiazine in 100 ml of dioxane, 7.5 ml of triethylamine and 7.0 ml of benzoylchloride were added, and the mixture was heated under reflux for 28 hours. Water was added to the reaction solution, and the mixture was extracted with dichloromethane. Combined organic solution was washed with dilute hydrochloric acid, saturated aqueous sodium bicarbonate, and saturated aqueous sodium chloride successively, and the organic layer was dried over anhydrous sodium sulfate. The solvent was removed under reduced pressure. The resulting residue was purified by silica gel column chromatography, and the resulting crystals from the fraction of ethyl acetate-hexane (2: 1) were recrystallized with ethyl ether to obtain 3.92 g (yield: 62.3%) of the title compound.

Melting point: 154°–155° C.
FAB MS: 500 [M+H]$^+$
IR: $v^{KBr}$cm$^{-1}$: 1750, 1660, 1480, 1235, 1060
Optical rotation [α]$^{25}_D$–265.4° (c 1, CHCl$_3$)

EXAMPLE 22

(2R, 3R, 4S, 4aS, 10aR)-2-acetoxymethyl-10-benzyl -3, 4-diacetoxy-2, 3, 4, 4a, 10, 10a-hexahydropyrano [3, 2-b] [1, 4] benzothiazine (23)

The suspension of 610 mg of 2'-benzylaminophenyl 3, 4, 6-tri-O-acetyl-2-O-mesyl-1-thio-β-D-glucopyranoside, 600 mg of potassium acetate and 600 mg of sodium acetate trihydrate in 15 ml of 90% ethanol was heated under reflux for two hours. The reaction solution was concentrated under reduced pressure, water was added to the resulting residue, and the mixture was extracted with dichlormethane. Combined organic solution was washed with saturated aqueous sodium chloride, and the organic layer was dried over anhydrous sodium sulfate. The solvent was removed under reduced pressure. The resulting residue was purified by silica gel column chromatography, and 190 mg (yield 35.3%) of the title compound was obtained from the fraction of ethyl acetate-hexane (2:1).

Melting point: 141°–144° C.
FAB MS: 485 [M]$^+$

IR: $\nu^{KBr}$cm$^{-1}$: 1750, 1730, 1590, 1490, 1240, 1050
Optical rotation $[\alpha]^{25}_D$+15.2° (c 1, CHCl$_3$)

EXAMPLE 23

(2R, 3S, 4S, 4aS, 10aR)-8-chloro-10-(2-diethylaminoethyl) -3,4-dihydroxy-2-tert-butyldiphenylsilyloxymethyl -2, 3, 4, 4a, 10, 10a-hexahydropyrano [3, 2-b] [1, 4] benzothiazine (24)

To the solution of 2.02 g of the compound (8) obtained in Example 8 in 20 ml of dimethylformamide, 0.68 g of imidazole and I ml of tert-butyldiphenylsilyl chloride was added, and the mixture was stirred overnight at room temperature. Methanol was added to the reaction solution, the mixture was extracted with ethyl acetate, and the organic layer was washed with water and saturated aqueous sodium chloride successively. The organic layer was dried over anhydrous magnesium sulfate, and the solvent was removed under reduced pressure to obtain the title compound.

NMR (CDCl$_3$): δ 0.97–1.04 (15H, m), 2.49–2.64 (6H, m), 3.35–3.71 (4H, m), 3.95–4.25 (6H, m), 4.90 (1H, s), 6.61 (1H, m), 6.74 (1H, d), 6.96 (1H, d), 7.26–7.58 (6H, m), 7.65 (4H, m)
FAB MS: 641 [M+H]$^+$

EXAMPLE 24

(2R, 3R, 4S, 4aS, 10aR)-8-chloro-10-(2-diethylaminoethyl) -3,4-dimethoxymethyloxy-2-hydroxymethyl -2, 3, 4, 4a, 10, 10a-hexahydropyrano [3, 2-b] [1, 4] benzothiazine (25)

To the solution of 3.00 g of the compound (24) obtained in Example 23 in 50 ml of a mixed solution of tetrahydrofuran-dimethylformamide (4:1), 600 mg of 60% oily sodium hydride and 1.17 ml of chloromethylmethyl ether were added, and the mixture was stirred for two hours at room temperature. The reacted solution was poured into water and the mixture was extracted with ethyl acetate. The organic layer was washed with water, and saturated aqueous sodium chloride successively, and was dried over anhydrous magnesium sulfate, and the solvent was removed under reduced pressure. To the solution of the resulting crude material in 75 ml of tetrahydrofuran, 9 ml of a 1M tetrabutylammonium-fluoride-tetrahydrofuran was added, and the solution was stirred overnight at room temperature. The reaction solution was concentrated, the residue was dissolved in ethyl acetate, and the solution was washed with water, and saturated aqueous sodium chloride successively. The organic layer was dried over anhydrous magnesium sulfate, and the solvent was removed under reduced pressure to obtain the title compound.

NMR (CDCl$_3$): δ 1.03 (6H, t), 2.5–2.7 (6H, m), 3.37–3.45 (7H, m), 3.65 (1H, m), 3.77–3.83 (2H, m), 3.89 (1H, m), 3.98 (1H, m), 4.06 (1H, m), 4.68 (1H, d), 4.74 (1H, d), 4.79 (1H, d), 4.87 (1H, d), 4.91 (1H, d), 6.64 (1H, m), 6.73 (1H, d), 6.98 (1H, d)

EXAMPLE 25

(2R, 3R, 4S, 4aS, 10aR)-8-chloro-10-(2-diethylaminoethyl) -3,4-dimethoxymethyloxy-2-methoxymethyl -2, 3, 4, 4a, 10, 10a-hexahydropyrano [3, 2-b] [1, 4] benzothiazine (26)

To the solution of 92 mg of the compound (25) obtained in Example 24 in 4.5 ml of a mixed solution of tetrahydrofuran-dimethylformamide (2:1), 30 mg of sodium hydride and 80 μl of methyl p-toluenesulfonate were added, and the mixture was stirred for five hours. After methanol was added to the solution, the mixture was poured into water and extracted with ethyl acetate. The organic layer was washed with water, and saturated aqueous sodium chloride successively and was dried over anhydrous magnesium sulfate. The solvent was removed under reduced pressure. The resulting residue was purified by silica gel column chromatography, and the title compound was obtained from the fraction of chloroformmethanol (19:1).

NMR (CDCl$_3$): δ 1.07 (6H, t), 2.60 (5H, m), 2.71 (1H, m), 3.37 (3H, s), 3.42–3.44 (7H, m), 3.54 (1H, m), 3.64 (1H, m), 3.70–3.75 (2H, m), 3.91 (1H, d), 4.03 (1H, m), 4.70–4.88 (5H, m), 6.62 (1H, m), 6.74 (1H, d), 6.98 (1H, d)

EXAMPLE 26

(2R, 3S, 4S, 4aS, 10aR)-8-chloro-10-(2-diethylaminoethyl) -3,4-dihydroxy-2-methoxymethyl-2, 3, 4, 4a, 10, 10a-hexahydropyrano [3, 2-b] [1, 4] benzothiazine (27)

The compound (26) 63 mg obtained in Example 25 was dissolved in 1 ml of methanol saturated with hydrogen chloride and 3 ml of methanol, and the solution was stirred for 2.5 hours at room temperature. The solution was concentrated under reduced pressure, the resulting residue was poured into 0.5N aqueous sodium hydroxide, and the mixture was extracted with ethyl acetate. The organic layer was washed with water, and saturated aqueous sodium chloride successively. The solution was dried over anhydrous magnesium sulfate. The solvent was removed under reduced pressure. The resulting residue was purified by NH-silica gel column chromatography (manufactured by Fuji Silicia Company), and 47.2 mg (yield 78.5%) of the title compound was obtained from the fraction of chloroform-methanol (19:1).

NMR (CDCl$_3$): δ 1.05 (6H, t), 2.59 (5H, m), 2.69 (1H, m), 3.39–3.42 (4H, m), 3.54 (1H, m), 3.62 (1H, m), 3.69–3.89 (5H, m), 4.01 (1H, m), 4.90 (1H, s), 6.62 (1H, m), 6.73 (1H, d), 6.98 (1H, d)
FAB MS: 417 [M+H]$^+$
Optical rotation $[\alpha]^{25}_D$–6.6° (c 0.9, CHCl$_3$)

EXAMPLE 27

According to the method of Example 25 except that methyl p-toluenesulfonate was changed to benzyl bromide, and the following compound was obtained.

(2R, 3R, 4S, 4aS, 10aR)-2-benzyloxymethyl -8-chloro-10-(2-diethylaminoethyl)-3,4-dimethoxymethyloxy -2, 3, 4, 4a, 10, 10a-hexahydropyrano [3, 2-b] [1, 4] benzothiazine (28)

NMR (CDCl$_3$): δ 1.04 (6H, t), 2.57 (4H, m), 2.59 (2H, m), 3.29 (3H, s), 3.44 (4H, m), 3.60 (1H, m), 3.70–3.83 (4H, m), 3.89 (1H, t), 4.02 (1H, m), 4.57 (2H, s), 4.66 (1H, d), 4.74–4.80 (3H, m), 4.87 (1H, s), 6.63 (1H, m), 6.77 (1H, d), 6.99 (1H, d), 7.26–7.30 (5H, m)
FAB MS: 581 [M+H]$^+$

EXAMPLE 28

According to the method of Example 26 except that compound (26) was changed to the compound (28) obtained in Example 27, and the following compound was obtained.

(2R, 3S, 4S, 4aS, 10aR)-2-benzyloxymethyl-8-chloro -10-(2-diethylaminoethyl)-3,4-dihydroxy-2, 3, 4, 4a, 10, 10a-hexahydropyrano [3, 2-b] [1, 4] benzothiazine (29)

NMR (CDCl$_3$): δ 1.07 (6H, t), 2.07 (4H, m), 2.86 (2H, m), 3.58 (1H, m), 3.70 (2H, m), 3.80 (2H, m), 3.89 (2H, m), 4.08 (1H, m), 4.50 (1H, d), 4.58 (1H, d), 5.00 (1H, s), 6.65 (1H, m), 6.72 (1H, d), 7.00 (1H, d), 7.30 (5H, m)

FAB MS: 493 [M+H]⁺

Optical rotation [α]$^{25}_D$–24.1° (c 1.5, CHCl₃)

EXAMPLE 29

According to the method of Example 25 except that methyl p-toluenesulfonate was changed to benzhydryl bromide, and the following compound was obtained.

(2R, 3R, 4S, 4aS, 10aR)-2-benzhydryloxymethyl-8-chloro-10-(2-diethylaminoethyl)-3,4-dimethoxymethyloxy -2, 3, 4, 4a, 10, 10a-hexahydropyrano [3, 2-b] [1, 4] benzothiazine (30)

NMR (CDCl₃): δ 1.00 (6H, t), 2.52 (6H, m), 2.71 (1H, m), 3.14 (3H, s), 3.60–4.00 (6H, m), 4.62 (11t, d), 4.73–4.79 (3H, m), 4.86 (1H, s), 5.48 (1H, s), 6.66 (1H, m), 6.80 (1H, d), 7.00 (1H, d), 7.17–7.43 (10H, m)

FAB MS: 657 [M+H]⁺

EXAMPLE 30

According to the method of Example 26 except that compound (26) was changed to the compound (30) obtained in Example 29, and the following compound was obtained.

(2R, 3S, 4S, 4aS, 10aR)-2-benzhydryloxymethyl-8-chloro-10-(2-diethylaminoethyl)-3,4-dihydroxy -2, 3, 4, 4a, 10, 10a-hexahydropyrano [3, 2-b] [1, 4] benzothiazine (31)

NMR (CDCl₃): δ 0.99 (6H, t), 2.50 (5H, m), 2.64 (1H, m), 3.20–3.40 (3H, m), 3.56–3.80 (5H, m), 3.93–3.97 (2H, m), 4.86 (1H, s), 5.47 (1H, s), 6.63 (1H, m), 6.73 (1H, d), 6.99 (1H, d), 7.21–7.30 (10H, m)

FAB MS: 569 [M+H]⁺

Optical rotation [α]$^{25}_D$–30.1° (c 0.8, CHCl₃)

EXAMPLE 31

According to the method of Example 25 except that methyl p-toluenesulfonate was changed to 4-fluorobenzyl bromide, and the following compound was obtained.

(2R, 3R, 4S, 4aS, 10aR)-8-chloro-10-(2-diethylaminoethyl) -3,4-dimethoxymethyloxy-2-(4-fluorobenzyl) oxymethyl -2, 3, 4, 4a, 10, 10a-hexahydropyrano [3, 2-b] [1, 4] benzothiazine (32)

NMR (CDCl₃): δ 1.04 (3H, t), 2.56 (6H, m), 2.71 (1H, m), 3.31 (3H, s), 3.44 (4H, m), 3.58 (1H, m), 3.70–3.80 (4H, m), 3.91 (1H, t), 4.02 (1H, m), 4.53 (2H, s), 4.66–4.87 (5H, m), 6.65 (1H, m), 6.76 (1H, d), 6.95–7.00 (3H, m), 7.26 (2H, m)

EXAMPLE 32

According to the method of Example 26 except that compound (26) was changed to the compound (32) obtained in Example 31, and the following compound was obtained.

(2R, 3S, 4S, 4aS, 10aR)-8-chloro-10-(2-diethylaminoethyl) -3,4-dihydroxy-2-(4-fluorobenzyl)oxymethyl -2, 3, 4, 4a, 10, 10a-hexahydropyrano [3, 2-b] [1, 4] benzothiazine (33)

NMR (CDCl₃): δ 1.02 (6H, t), 2.55(5H, m), 2.66 (1H, m), 3.40 (1H, m), 3.54 (1H, m), 3.60 (1H, m), 3.70–3.79 (5H, m), 3.89 (1H, t), 3.98 (1H, m), 4.48 (1H, d), 4.54 (1H, d), 4.87 (1H, s), 4.87 (1H, s), 6.63 (1H, m), 6.73 (1H, d), 6.98 (3H, m), 7.26 (2H, m)

FAB MS: 511 [M+H]⁺

Optical rotation [α]$^{25}_D$–20.1° (c, 0.9, CHCl₃)

EXAMPLE 33

According to the method of Example 23 except that tert-butyldiphenylsilyl chloride was changed to trityl bromide, and the following compound was obtained.

(2R, 3S, 4S, 4aS, 10aR)-8-chloro-10-(2-diethylaminoethyl) -3,4-dihydroxy-2-trityloxymethly -2, 3, 4, 4a, 10, 10a-hexahydropyrano [3, 2-b] [1, 4] benzothiazine (34)

NMR (CDCl₃): δ 1.00 (6H, t), 2.50–2.70 (6H, m), 3.30–3.40 (2H, m), 3.51 (2H, m), 3.65 (2H, m), 3.93 (1H, t), 4.01 (1H, m), 4.90 (1H, s), 6.61 (1H, m), 6.73 (1H, d), 6.78 (1H, d), 7.21–7.29 (10H, m), 7.41 (6H, m)

Optical rotation [α]$^{25}_D$–44.0° (c 14, CHCl₃)

EXAMPLE 34

(2R, 3S, 4S, 4aS, 10aR)-8-chloro-10-(2-diethylaminoethyl) -3, 4-dihydroxy-2-[tris (4-methoxyphenyl) methyloxymethyl]-2, 3, 4, 4a, 10, 10a-hexahydropyrano [3, 2-b] [1, 4] benzothiazine (35)

To the solution of 202 mg of the compound (8) obtained in Example 8 in 2 ml of pyridine, 200 mg of tris (4-methoxyphenyl) methylchloride was added, and the solution was stirred overnight at room temperature. The reaction mixture was poured into ice water, the mixture was extracted with ethyl acetate, and the organic layer was washed with water, 2N hydrochloric acid, and saturated aqueous sodium bicarbonate successively. The solution was dried over anhydrous magnesium sulfate, and the solvent was removed under reduced pressure. The resulting residue was purified by silica gel column chromatography to obtain 46.6 mg (yield 12.6%) of the title compound.

NMR (CDCl₃): δ 1.02 (6H, t), 2.56–2.80 (8H, m), 3.36–3.52 (4H, m), 3.69–3.79 (11H, m), 3.94–4.06 (2}}, m), 4.93 (1H, s), 6.64 (1H, m), 6.73 (1H, d), 6.78 (6H, d), 7.99 (1H, d), 7.27 (6H, d)

FAB MS: 735 [M+H]⁺

Optical rotation [α]$^{25}_D$–36.7° (c 0 8, CHCl₃)

EXAMPLE 35

(2R, 3R, 4S, 4aS, 10aR)-8-chloro-3, 4-diacetoxy-10 -(2-diethylaminoethyl)-2-(4-methylphenylsulfonyloxy) -2, 3, 4, 4a, 10, 10a-hexahydropyrano [3, 2-b] [1, 4] benzothiazine (36)

To the solution of 1.0 g of the compound (8) obtained in Example 8 in 10 ml of pyridine, 780 mg of p-toluene sulfonylchloride was added, and the solution was stirred overnight at 4° C. After 5 ml of acetic anhydride was added, the reaction mixture was stirred for 3 hours at 0° C. The reaction solution was poured into ice water, the mixture was extracted with ethyl acetate, and the organic layer was washed with diluted hydrochloric acid, and a saturated aqueous sodium bicarbonate successively. The solution was dried over anhydrous magnesium sulfate, and the solvent was removed under reduced pressure, and 1.47 g (yield 92.7%) of the title compound was obtained.

NMR (CDCl₃): δ 1.05 (3H, t), 2.04 (3H, s), 2.09 (3H, s), 2.36 (3H, s), 2.48–2.62 (7H, m), 3.30–3.40 (1H, m), 3.60 (1H, m), 3.81 (2H, m), 4.04–4.10 (3H, m), 4.97 (1H, d), 5.21–5.28 (2H, m), 6.65 (1H, m), 6.72 (1H, d), 6.94 (1H, d), 7.19 (2H, d), 7.70 (2H, d)

EXAMPLE 36

(2R, 3R, 4S, 4aS, 10aR)-2-azidomethyl-8-chloro -3, 4-diacetoxy-10-(2-diethylaminoethyl)-2, 3, 4, 4a, 10, 10a-hexahydropyrano [3, 2-b] [1, 4] benzothiazine (37)

To the solution of 14.0 g of the compound (36) obtained in Example 35 in 140 ml of dimethylsulfoxide, 14.0 g of sodium azide was added, and the mixture was heated with stirring for 45 minutes at 100 ° C. The reaction solution was poured into ice water, the mixture was extracted with ethyl acetate, and the organic layer was washed with saturated aqueous sodium chloride. The solution was dried over anhydrous magnesium sulfate, and the solvent was removed under reduced pressure. The resulting residue was purified by silica gel column chromatography to obtain 10.1 g (yield 90.2%) of the title compound from the fraction of chloroform-acetone (1:1).

NMR (CDCl$_3$): δ 1.08 (6H, t), 2.02 (3H, s), 2.07 (3H, s), 2.58–2.80 (6H, m), 3.25 (1H, m), 3.41 (1H, m), 3.55 (1H, m), 3.75 (2H, m), 3.84 (1H, m), 5.15 (1H, d), 5.25 (1H, m), 5.31 (1H, m), 6.65 (1H, m), 6.74 (1H, d), 6.97 (1H, d)

FAB MS: 511 [M+H]$^+$

EXAMPLE 37

(2R, 3S, 4S, 4aS, 10aR)-2-azidomethyl-8-chloro-10-(2diethylaminoethyl) -3, 4-dihydroxy-2, 3, 4, 4a, 10, 10a-hexahydropyrano [3, 2-b] [1, 4] benzothiazine (38)

The compound (37) 10.1 g obtained in Example 36 was dissolved in 250 ml of ammonia-saturated methanol, and the solution was stirred for 6 hours at room temperature. The solvent was removed under reduced pressure to obtain the title compound quantitatively.

NMR (DMSO-d$_6$): δ 0.98 (6H, t), 2.50–2.60 (6H, m), 3.30–3.60 (6H, m), 3.64 (1H, m), 3.86 (1H, m), 5.06 (2H, m), 5.41 (1H, d), 6.63 (1H, m), 6.74 (1H, d), 6.97 (1H, d)

FAB MS: 428 [M+H]$^+$

EXAMPLE 38

(2R, 3R, 4S, 4aS, 10aR)-2-azidomethyl-8-chloro-10 -(2-diethylaminoethyl)-3, 4-(1, 1, 3, 3-tetraisopropyldisiloxane -1, 3-diyldioxy)-2, 3, 4, 4a, 10, 10a-hexahydropyrano [3, 2-b] [1, 4] benzothiazine (39)

To the solution of 3.7 g of the compound (38) obtained in Example 37 in 75 ml of dimethylformamide, 2.98 g of imidazole and 5.45 g of 1,3-dichloro-1, 1, 3, 3-tetraisopropyldisiloxane were added, and the mixture was heated with stirring for 4 hours at 60° C. The reaction solution was poured into ice water, the mixture was extracted with diethyl ether, and the organic layer was washed with diluted hydrochloric acid, and saturated aqueous sodium bicarbonate successively. The solution was dried over anhydrous magnesium sulfate, and the solvent was removed under reduced pressure. The resulting residue was purified by silica gel column chromatography to obtain 5.26 g (yield 90.7%) of the title compound from the fraction of hexane-ethyl acetate (3:2).

NMR (CDCl$_3$): δ 0.90–1.50 (34H, m), 2.54–2.63 (4H, m), 2.07–2.73 (2H, m), 3.44–3.48 (2H, m), 3.65–3.75 (1H, m), 3.75 (1H, m), 4.00 (1H, m), 4.09 (1H, m), 4.97 (1H, d), 6.64 (1H, m), 6.74 (1H, d), 7.00 (1H, d)

FAB MS: 669 [M+H]$^+$

EXAMPLE 39

(2R, 3R, 4S, 4aS, 10aR)-2-aminomethyl-8-chloro-10 -(2-diethylaminoethyl)-3, 4-(1, 1, 3, 3-tetraisopropyldisiloxane -1, 3-diyldioxy)-2, 3, 4, 4a, 10, 10a-hexahydropyrano [3, 2-b] [1, 4] benzothiazine (40)

To the solution of 3.29 g of the compound (39) obtained in Example 38 in 70 ml of ethanol, 700 mg of a Lindler catalyst was added, and the mixture was heated with stirring overnight at room temperature in an atmosphere of hydrogen. The catalyst was filtered off, and the solvent was removed under reduced pressure to obtain the title compound quantitatively.

NMR (CDCl$_3$): δ 1.01–1.10 (34H, m), 2.53–2.75 (6H, m), 2.86–2.90 (1H, m), 3.12–3.15 (1H, m), 3.33 (1H, m), 3.40–3.50 (1H, m), 3.65–3.75 (2H, m), 3.90–3.94 (1H, m), 4.08–4.10 (1H, m), 4.91 (1H, d), 6.63 (1H, m), 6.64 (1H, d), 7.00 (1H, d)

FAB MS: 643 [M+H]$^+$

EXAMPLE 40

(2R, 3R, 4S, 4aS, 10aR)-2-benzylaminomethyl-8-chloro -10(2-diethylaminoethyl)-3, 4-(1, 1, 3, 3-tetraisopropyldisiloxane -1, 3-diyldioxy)-2, 3, 4, 4a, 10, 10a-hexahydropyrano [3, 2-b] [1, 4] benzothiazine (41)

To the solution of 418 mg of the compound (40) obtained in Example 39 in 10 ml of chloroform, 1.8 ml of triethylamine and 0.77 ml of benzyl bromide were added, and the mixture was heated with stirring overnight at room temperature. The reaction solution was poured into ice water, the mixture was extracted with methylene chloride, and the organic layer was washed with diluted hydrochloric acid, saturated aqueous sodium bicarbonate, and saturated aqueous sodium chloride successively. The solution was dried over anhydrous magnesium sulfate, and the solvent was removed under reduced pressure. The resulting residue was purified by silica gel column chromatography to obtain 0.19 mg (yield 39.4%) of the title compound from the fraction of chloroform-methanol (19:1).

NMR (CDCl$_3$): δ 0.98–1.10 (34H, m), 2.40–2.60 (5H, m), 2.63–2.73 (1H, m), 2.80–2.86 (1H, m), 3.06 (1H, m), 3.40 (1H, m), 3.55 (1H, m), 3.66 (1H, m), 3.71 (1H, m), 3.77 (2H, m), 3.95 (1H, m), 4.07 (1H, m), 4.88 (1H, m), 6.62 (1H, m), 6.73 (1H, d), 7.00 (1H, d), 7.20–7.30 (5H, m)

FAB MS: 773 [M+H]$^+$

EXAMPLE 41

(2R, 3S, 4S, 4aS, 10aR)-2-benzylaminomethyl-8-chloro -10-(2-diethylaminoethyl)-3, 4-dihydroxy -2, 3, 4, 4a, 10, 10a-hexahydropyrano [3, 2-b] [1, 4] benzothiazine (42)

To the solution of 100 mg of the compound (41) obtained in Example 40 in 2 ml of tetrahydrofuran, 100 μl of a 1M tetrabutylammoniumfluoride-tetrahydrofuran solution was added, and the mixture was stirred for 5 minutes. The reaction solution was poured into water, the mixture was extracted with ethyl acetate, and the organic layer was washed with saturated aqueous sodium chloride. The solution was dried over anhydrous magnesium sulfate, and the solvent was removed. The resulting residue was purified by NH-silica gel column chromatography to obtain 65 mg (yield 97.1%) of the title compound from the fraction of chloroform-methanol (19:1).

NMR (CDCl$_3$): δ 0.99 (6H, t), 2.45–2.70 (6H, m), 2.94–3.0 (2H, m), 3.36–3.40 (1H, m), 3.47–3.52 (1H, m), 3.56 (1H, m), 3.67–3.81 (4H, m), 3.97 (1H, m), 4.88 (1H, bs), 6.61 (1H, m), 6.70 (1H, d), 6.96 (1H, d), 7.22–7.30 (5H, m)

FAB MS: 491 [M+H]+

Optical rotation [α]$^{25}_D$–20.9° (c 1.3, CHCl$_3$)

EXAMPLE 42

(2R, 3R 4S, 4aS, 10aR)-2-benzhydrylaminomethyl-8-chloro-10-(2-diethylaminoethyl)-3, 4-(1, 1, 3, 3-tetraisopropyl-disiloxane -1, 3-diyldioxy)-2, 3, 4, 4a, 10, 10a-hexahydropyrano [3, 2-b] [1, 4] benzothiazine (43)

To the solution of 280 mg of the compound (40) obtained in Example 39 in 3 ml of acetonitrile, 0.6 ml of triethylamine and 536 mg of benzhydryl bromide were added, and the mixture was stirred overnight at room temperature. The reaction solution was poured into ice water, the mixture was extracted with ethyl acetate, and the organic layer was washed with diluted hydrochloric acid, saturated aqueous sodium bicarbonate, and saturated aqueous sodium chloride successively. The solution was dried over anhydrous magnesium sulfate, and the solvent was removed under reduced pressure. The resulting residue was purified by silica gel column chromatography to obtain 0.20 mg (yield 55.4%) of the title compound from the fraction of hexane-ethyl acetate (2:1).

NMR (CDCl$_3$): δ 0.85–1.10 (34H, m), 2.40 (2H, m), 2.48 (2H, m), 2.53 (1H, m), 2.63–2.78 (2H, m), 2.99 (1H, m), 3.35–3.41 (1H, m), 3.55–3.59 (1H, m), 3.65–3.72 (2H, m), 3.86 (1H, m), 4.06 (1H, m), 4.79 (1H, s), 4.89 (1H, d), 6.63 (1H, m), 6.72 (1H, d), 6.99 (1H, d), 7.15 (2H, m), 7.25 (4H, m), 7.30–7.40 (4H, m)

FAB MS: 809 [M+H]+

EXAMPLE 43

According to the method of Example 41 except that the compound (43) obtained in Example 42 was used, and the following compound was obtained.

(2R, 3S, 4S, 4aS, 10aR )-2-benzhydrylaminomethyl-8-chloro -10-(2-diethylaminoethyl)-3, 4-dihydroxy -2, 3, 4, 4a, 10, 10a-hexahydropyrano [3, 2-b] [1, 4] benzothiazine (44)

NMR (CDCl$_3$): δ 0.96 (6H, t), 2.40–2.60 (5H, m), 2.62 (1H, m), 2.91 (2H, m), 3.34 (1H, m), 3.44 (1H, m), 3.55 (1H, m), 3.65 (1H, m), 3.83 (1H, m), 3.95 (1H, m), 4.78 (1H, s), 4.83 (1H, d), 6.61 (1H, m), 6.70 (1H, d), 6.95 (1H, d), 7.17–7.33 (10H, m)

FAB MS: 567 [M+H]+

Optical rotation [α]$^{25}_D$–28.7° (c 1.24, CHCl$_3$)

EXAMPLE 44

According to the method of Example 40 except that benzyl bromide was changed to trityl bromide, and the following compound was obtained.

(2R, 3R, 4S, 4aS, 10aR)-8-chloro-10-(2-diethylaminoethyl) -3, 4-(1, 1, 3, 3-tetraisopropyldisiloxane-1, 3 -diyldioxy)-2-tritylaminomethyl-2, 3, 4, 4a, 10, 10a-hexahydropyrano [3, 2-b] [1, 4] benzothiazine (45)

NMR (CDCl$_3$): δ 0.74–1.08 (34H, m), 2.18 (1H, m), 2.53–2.82 (7H, m), 3.50 (1H, m), 3.59 (1H, m), 3.67–3.80 (3H, m), 4.08 (1H, m), 4.97 (1H, d), 6.60 (1H, m), 6.74 (1H, d), 6.95 (1H, d), 7.12–7.23 (9H, m), 7.42 (6H, m)

EXAMPLE 45

According to the method of Example 41 except that the compound (45) obtained in Example 44 was used, and the following compound was obtained.

(2R, 3S, 4S, 4aS, 10aR)-8-chloro-10-(2-diethylaminoethyl) -3, 4-dihydroxy-2-tritylaminomethyl -2, 3, 4, 4a, 10, 10a-hexahydropyrano [3, 2-b] [1, 4] benzothiazine (46)

NMR (CDCl$_3$): δ 0.97 (6H, t), 2.50 (6H, m), 2.65 (1H, m), 2.73 (1H, m), 3.30–3.38 (2H, m), 3.59 (1H, m), 3.67 (1H, m), 4.01 (2H, m), 4.84 (1H, d), 6.59 (1H, m), 6.70 (1H, d), 6.95 (1H, d), 7.16 (3H, m), 7.24 (6H, m), 7.38 (6H, m)

FAB MS: 643 [M+H]+

Optical rotation [α]$^{25}_D$4.7° (c 1.2, CHCl$_3$)

EXAMPLE 46

According to the method of Example 42 except that the compound (40) obtained in Example 39 was used, and that benzhydryl bromide was changed to benzyl bromide, and the following compound was obtained.

(2R, 3R, 4S, 4aS, 10aR)-8-chloro-2-dibenzylaminomethyl -10-(2-diethylaminoethyl)-3, 4-(1, 1, 3, 3-tetraisopropyldisiloxane -1, 3-diyldioxy)-2, 3, 4, 4a, 10, 10a-hexahydropyrano [3, 2-b] [1, 4] benzothiazine (47)

NMR (CDCl$_3$): δ 0.79–1.1 (34H, m), 2.2–2.55 (4H, m), 2.60–2.70 (3H, m), 3.08 (1H, m), 3.42 (1}], m), 3.52–3.62 (4H, m), 3.70–3.78 (2H, m), 3.92 (2H, m), 4.02 (1H, m), 4.94 (1H, d), 6.62 (1H, m), 6.70 (1H, d), 7.16–7.26 (6H, m), 7.34 (4H, m)

FAB MS: 823 [M+H]+

EXAMPLE 47

According to the method of Example 41 except that the compound (47) obtained in Example 46 was used, and the following compound was obtained.

(2R, 3S, 4S, 4aS, 10aR)-8-chloro-2-dibenzylaminomethyl -10-(2-diethylaminoethyl)-3, 4-dihydroxy-2, 3, 4, 4a, 10, 10a-hexahydropyrano [3, 2-b] [1, 4] benzothiazine (48)

NMR (CDCl$_3$): δ 1.05 (6H, t), 2.50–2.70 (6H, m), 2.76 (1H, m), 2.98 (1H, m), 3.37 (2H, m), 3.45 (1H, m), 3.57 (1H, m), 3.61–3.70 (2H, m), 3.87 (2H, m), 4.01 (1H, m), 4.87 (1H, bs), 6.59 (1H, m), 6.70 (1H, d), 6.95 (1H, d), 7.25–7.34 (10H, m)

FAB MS: 581 [M+H]+

Optical rotation [α]$^{25}_D$–86.8° (c 1.3, CHCl$_3$)

EXAMPLE 48

According to the method of Example 42 except that benzhydryl bromide was changed to 5-chlorodibenzosuberan, and the following compound was obtained.

(2R, 3R, 4S, 4aS, 10aR)-8-chloro-10-(2-diethylaminoethyl) -2-[(10, 11-dihydro-5H-dibenzo [a, d] cycloheptene-5-yl) aminomethyl]-3, 4-(1, 1, 3, 3-tetraisopropyldisiloxane-1, 3 -diyldioxy)-2, 3, 4, 4a, 10, 10a-hexahydropyrano [3, 2-b] [1,4] benzothiazine (49)

NMR (CDCl$_3$): δ 0.79–1.1 (34H, m), 2.30–2.50 (5H, m), 2.60–2.75 (2H, m), 2.75–2.95 (3H, m), 3.32 (1H, m), 3.45 (1H, m), 3.60–3.70 (3H, m), 3.83 (1H, m), 3.95–4.04 (2H, m), 4.70 (1H, bs), 4.83 (1H, d), 6.62 (1H, m), 6.71 (1H, d), 6.99 (1H, d), 7.03–7.20 (8H, m)

FAB MS: 835 [M+H]+

EXAMPLE 49

According to the method of Example 41 except that the compound (49) obtained in Example 48 was used, and the following compound was obtained.

(2R, 3S, 4S, 4aS, 10aR)-8-chloro-10-(2-diethylaminoethyl) -2-[(10, 11-dihydro-5H-dibenzo [a, d] cycloheptene -5-yl) aminomethyl]-3, 4-dihydroxy-2, 3, 4, 4a, 10, 10a -hexahydropyrano [3, 2-b] [1, 4] benzothiazine (50)

NMR (CDCl$_3$): δ 0.96 (6H, t), 2.40–2.54 (5H, m), 2.62 (1H, m), 2.86–3.00 (4H, m), 3.30–3.46 (4H, m), 3.56 (1H, m), 3.65 (1H, m), 3.72 (1H, m), 3.82 (1H, m), 4.74 (2H, bs), 6.60 (1H, m), 6.70 (1H, d), 6.94 (1H, d), 7.05–7.22 (8H, m)

FAB MS: 593 [M+H]$^+$

Optical rotation [α]$^{25}_D$–19.4° (c 2.0, CHCl$_3$)

EXAMPLE 50

(2R, 3R, 4S, 4aS, 10aR)-2-acetylthio-8-chloro-3, 4 -diacetoxy-10-(2-diethylaminoethyl)-2, 3, 4, 4a, 10, 10a- hexahydropyrano [3, 2-b] [1, 4] benzothiazine (51)

To the solution of 2.0 g of the compound (36) obtained in Example 35 in 100 ml of acetone, 1.0 g of potassium thioacetate was added, and the mixture was heated with refluxing for 6.5 hours. The solvent was removed under reduced pressure, and the residue was dissolved in ethyl acetate. The organic layer was washed with water and dried over anhydrous magnesium sulfate. The solvent was removed under reduced pressure to obtain 1.65 g (yield 96.8% ) of the title compound.

NMR (CDCl$_3$): δ 1.06 (6H, t), 2.08 (3H, s), 2.10 (3H, s), 2.30 (3H, s), 2.62 (4H, m), 2.72 (2H, m), 2.91 (1H, m), 3.32 (1H, m), 3.41 (1H, m), 3.58 (1H, m), 3.70 (1H, m), 3.81 (1H, m), 4.98 (1H, d), 5.22 (1H, m), 5.30 (1H, m), 6.64 (1H, m), 6.73 (1H, d), 6.97 (1H, d)

FAB MS: 545 [M+H]$^+$

EXAMPLE 51

(2R, 3S, 4S, 4aS, 10aR)-8-chloro-10-(2-diethylaminoethyl) -3, 4-dihydroxy-2-mercaptomethyl-2, 3, 4, 4a, 10, 10a- hexahydropyrano [3, 2-b] [1, 4] benzothiazine (52)

The compound (51) 1.2 g obtained in Example 50 was dissolved in 60 ml of ammonia-saturated methanol, and the mixture was stirred for 2.5 hours at room temperature. The solvent was removed under reduced pressure, and the title compound was obtained quantitatively.

NMR (CDCl$_3$): δ 1.04 (6H, t), 2.61(4H, m), 2.73 (3H, m), 2.98 (1H, m), 3.43 (2H, m), 3.62 (1H, m), 3.76 (2H, m), 4.01 (1H, m), 4.89 (1H, d), 6.58 (1H, m), 6.69 (1H, d), 6.89 (1H, d)

FAB MS: 419 [M+H]$^+$

Optical rotation [α]$^{25}_D$–8.4° (c 2.0, CH$_3$OH)

EXAMPLE 52

(2S, 3S, 4S, 4aS, 10aR)-8-chloro-10-(2-diethylaminoethyl) -3, 4-dihydroxy-2-methylthiomethyl-2, 3, 4, 4a, 10, 10a- hexahydropyrano [3, 2-b] [1, 4] benzothiazine (53)

To the solution of 1.0 g of the compound (51) obtained in Example 50 in 50 ml of methanol, 300 mg of sodium methylate was added, and the mixture was stirred for 15 minutes at room temperature. Then, 1 ml of methyl iodide was added, and the mixture was stirred for 45 minutes at room temperature. The solvent was removed under reduced pressure, and the residue was dissolved in ethyl acetate. The organic layer was washed with saturated aqueous sodium chloride and dried over anhydrous magnesium sulfate. The solvent was removed under reduced pressure. The resulting residue was purified by silica gel column chromatography to obtain 0.33 g (yield 41.6% ) of the title compound from the fraction of chloroformmethanol (9:1).

NMR (CDCl$_3$): δ 1.07 (6H, t), 2.13 (3H, s), 2.60–2.82 (7H, m), 2.98 (1H, m), 3.41 (1H, m), 3.56 (1H, m), 3.65 (1H, m), 3.77 (1H, m), 3.84 (1H, m), 4.03 (1H, m), 4.89 (1H, bs), 6.61 (1H, m), 6.72 (1H, d), 6.94 (1H, d)

FAB MS: 432 [M+H]$^+$

Optical rotation [α]$^{25}_D$+23.6° (c, 10, CHCl$_3$)

EXAMPLE 53

According to the method of Example 52 except that methyl iodide was changed to benzyl bromide, and the following compound was obtained.

(2S, 3S 4S 4aS 10aR) 2-benzylthiomethyl 8-chloro -10- (2-diethylaminoethyl))-3, 4-dihydroxy-2, 3, 4, 4a, 10, 10a- hexahydropyrano [3, 2-b] [1, 4] benzothiazine (54)

NMR (CDCl$_3$): δ 1.04 (6H, t), 2.50–2.70 (6H, m), 2.77 (1H, m), 2.91 (1H, m), 3.40 (1H, m), 3.54 (1H, m), 3.65–3.80 (4H, m), 3.88 (1H, m), 4.00 (1H, m), 4.84 (1H, d), 6.60 (1H, m), 6.72 (1H, d), 6.92 (1H, d), 7.18 (5H, m)

FAB MS: 509 [M+H]$^+$

Optical rotation [α]$^{25}_D$+14.4° (c 1.0, CHCl$_3$)

EXAMPLE 54

According to the method of Example 52 except that methyl iodide was changed to benzhydryl bromide, and the following compound was obtained.

(2S, 3S, 4S, 4aS, 10aR)-2-benzhydrylthiomethyl-8-chloro -10-(2-diethylaminoethyl)-3, 4-dihydroxy-2, 3, 4, 4a, 10, 10a-hexahydropyrano [3, 2-b] [1, 4] benzothiazine (55)

NMR (CDCl$_3$): δ 0.98 (6H, t), 2.50–2.70 (7H, m), 2.81 (1H, m), 3.38 (1H, m), 3.56 (1H, m), 3.66 (1H, m), 3.76 (1H, m), 4.00 (1H, m), 4.08 (1H, m), 4.81 (1H, d), 5.36 (1H, s), 6.65 (1H, m), 6.73 (1H, d), 6.98 (1H, d), 7.11–7.26 (10H, m)

FAB MS: 585 [M+H]$^+$

[α]$^{25}_D$–9.3° (c 1.0, CHCl$_3$)

EXAMPLE 55

(2S, 3S, 4S, 4aS, 10aR)-8-chloro-10-(2-diethylaminoethyl) 3, 4-dihydroxy-2-tritylthiomethyl-2, 3, 4, 4a, 10, 10a- hexahydropyrano [3, 2-b] [1, 4] benzothiazine (56)

To the solution of 4.03 g of (2R, 3S, 4S, 4aS, 10aR)-8- chloro-10-(2-diethylaminoethyl)-3, 4-dihydroxy -2-hydroxymethyl-2, 3, 4, 4a, 10, 10a-hexahydropyrano [3, 2-b] [1, 4] benzothiazine in 80 ml of pyridine, 3.9 g of trityl bromide was added, and the mixture was stirred overnight at room temperature. The reaction solution was poured into water and extracted with chloroform. The organic layer was washed with diluted hydrochloric acid, saturated aqueous sodium bicarbonate and saturated aqueous sodium chloride successively, and dried over anhydrous magnesium sulfate. The solvent was removed under reduced pressure. The resulting residue was purified by silica gel column chromatography to obtain 1.19 g (yield 18.4%) of the title compound from the fraction of chloroform-methanol (19:1).

NMR (CDCl$_3$): δ 0.97 (6H, t), 2.50–2.70 (7H, m), 2.82 (1H, m), 3.04 (1H, m), 3.32 (1H, m), 3.45–3.50 (2H, m), 3.71–3.80 (2H, m), 4.66 (1H, bs), 6.59 (1H, m), 6.73 (1H, d), 6.92 (1H, d), 7.16–7.25 (9H, m), 7.39 (6H, m)

FAB MS: 661 [M+H]$^+$

Optical rotation [α]$^{25}_D$–19.1° (c 1.0, CHCl$_3$)

EXAMPLE 56

According to the method of Example 52 except that methyl iodide was changed to phenetyl bromide, and the following compound was obtained.

(2S, 3S, 4S, 4aS, 10aR)-8-chloro-10-(2-diethylaminoethyl) 3, 4-dihydroxy-2-phenetylthiomethyl-2, 3, 4, 4a, 10, 10a-hexahydropyrano [3, 2-b] [1, 4] benzothiazine (57)

NMR (CDCl$_3$): δ 1.02 (6H, t), 2.55 (4H, m), 2.64 (1H, m), 2.73 (1H, m), 2.82 (5H, m), 3.04 (1H, m), 3.37 (1H, m), 3.57 (1H, m), 3.66 (1H, m), 3.72 (1H, m), 3.95 (1H, m), 4.02 (1H, m), 4.86 (1H, d), 6.60 (1H, m), 6.71 (1H, d), 6.93 (1H, d), 7.01 (2H, m), 7.16 (3H, m)

FAB MS: 523 [M+H]$^+$

Optical rotation $[\alpha]^{25}{}_D$+28.6° (c 1.0, CHCl$_3$)

EXAMPLE 57

According to the method of Example 52 except that methyl iodide was changed to 4-fluorobenzyl bromide, and the following compound was obtained.

(2S, 3S, 4S, 4aS, 10aR)-8-chloro-10-(2-diethylaminoethyl) 3, 4-dihydroxy-2-(4-fluorobenzylthiomethyl)-2, 3, 4, 4a, 10, 10a-hexahydropyrano [3, 2-b] [1, 4] benzothiazine (58)

NMR (CDCl$_3$): δ 1.06 (6H, t), 2.55–2.80 (7H, m), 2.87 (1H, m), 3.45 (1H, m), 3.55 (1H, m), 3.70–3.80 (4H, m), 3.94 (1H, m), 4.03 (1H, m), 4.91 (1H, d), 6.64 (1H, m), 6.74 (1H, d), 6.91 (2H, m), 6.98 (1H, d), 7.16 (2H, m)

FAB MS: 526 [M+H]$^+$

Optical rotation $[\alpha]^{25}{}_D$+20.0° (c 1.0, CHCl$_3$)

EXAMPLE 58

(2S, 3S, 4S, 4aS, 10aR)-8-chloro-10-(2-diethylaminoethyl) 3, 4-dihydroxy-2-phenylthiomethyl-2, 3, 4, 4a, 10, 10a-hexahydropyrano [3, 2-b] [1, 4] benzothiazine (59)

To the solution of 105 mg of the compound (8) obtained in Example 8 in 2 ml of pyridine, 120 mg of diphenyldisulfide and 0.15 ml of tri-n-butylphosphine were added, and the mixture was heated with stirring for one hour at 90° C. The reaction solution was diluted with ethyl acetate, and the mixture was washed with 40% aqueous potassium hydroxide, water, and saturated aqueous sodium chloride successively. The organic layer was dried over anhydrous magnesium sulfate, and the solvent was removed under reduced pressure. The resulting residue was purified by silica gel column chromatography, and 113 mg (yield: 87.4%) of the title compound was obtained from the fraction of chloroform-methanol (9:1).

NMR (CDCl$_3$): δ 1.05 (6H, t), 2.63 (5H, m), 2.80 (1H, m), 3.11 (1H, m), 3.36 (1H, m), 3.49 (1H, m), 3.56 (1H, m), 3.65 (1H, m), 3.77 (1H, m), 3.85 (1H, m), 3.97 (1H, m), 4.83 (1H, d), 6.60 (1H, m), 6.71 (1H, d), 6.93 (1H, d), 7.16 (2H, m), 7.30 (2H, m)

FAB MS: 495 [M+H]$^+$

Optical rotation $[\alpha]^{25}{}_D$+58.9° (c 2.2, CHCl$_3$)

EXAMPLE 59

(2S, 3S, 4S, 4aS, 10aR)-8-chloro-10-(2-diethylaminoethyl) 3, 4-dihydroxy-2-trityloxymethyl-2, 3, 4, 4a, 10, 10a-hexahydropyrano [3, 2-b] [1, 4] benzothiazine hydrochloride ½ hydrate (60)

To the solution of 500 mg of the compound (34) obtained in Example 33 in 3 ml of acetone, 1.5 ml of hydrochloric acid-saturated diethyl ether was added at 0° C., and the mixture was stirred for 10 minutes. The precipitate was filtered to obtain 440 mg (yield 82.2%) of the title compound.

Melting point: 180°–182° C.

| Anal. Calcd. for C$_{37}$H$_{41}$ClO$_4$N$_2$S.HCl.½H$_2$O | | | |
|---|---|---|---|
| | C (%) | H (%) | N (%) |
| Calcd: | 64.34 | 6.27 | 4.06 |
| Found: | 64.61 | 6.39 | 4.11 |

NMR (CDCl$_3$): δ 1.05–1.12 (6H, m), 3.00–3.15 (8H, m), 3.57–3.65 (2H, m), 3.82–3.86 (3H, m), 4.07 (1H, m), 4.81 (1H, m), 5.15 (1H, bs), 5.39 (1H, m), 6.70 (1H, m), 7.03 (2H, d), 7.22 (9H, m), 7.36 (6H, m), 10.44 (1H, bs)

About representative compounds of hexahydropyrano [3, 2-b] [1, 4] benzothiazine derivative (I) obtained in Examples 1–59, facilitated activity for metabolic turnover of inositol phospholipid in vitro was determined by the following method.

The preparation of slice samples of a rat hippocampus and the experiments of metabolic turnover of inositol phospholipids were performed according to a method of Y. Nakagawa and M. Baudry [Neuroscience, vol. 32, pp. 363–369 (1989)]. Transverse slices (400 μm) were obtained with a McIlwain tissue chopper. The hippocampus slices were incubated in a Krebs-bicarbonate medium (114 mM NaCl, 5.5 mM KCl, 0.75 mM CaCl$_2$, 1.2 mM Na$_2$HPO$_4$, 1.2 mM MgCl$_2$, 20 mM NaHCO$_3$, 10 mM glucose) containing 3H-myo-inositol (15 μCi/ml) for 100 minutes with aeration of O$_2$/CO$_2$ (95:5) at 37° C., and the labeled slices and the above materials to be tested (300 μM) were reacted for 60 minutes in the presence of 10 mM LiCl. After the reaction was stopped with 6% TCA, the fractions of inositolphospholic acid (IP$_1$) were separated according to a method of Berridge et al [Biochem. J., vol. 206, pp. 587–595 (1982)], and the radioactivity was determined. The numerical value is shown by the basal value of 100. The results are shown in Table 1.

TABLE 1

| Compound (300 μM) | Response (%) |
|---|---|
| Compound 31 | 230 |
| Compound 44 | 330 |
| Compound 48 | 200 |
| Compound 54 | 280 |
| Compound 55 | 320 |
| Compound 57 | 200 |

We claim:

1. A compound of formula (I) or a pharmaceutically acceptable acid-addition salt thereof:

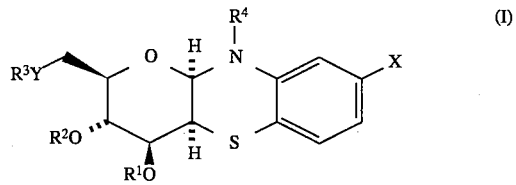

wherein

R$^1$ and R$^2$ are identical or different, and R$^1$ and R$^2$ each can be hydrogen, a lower acyl, benzoyl, or lower alkoxyalkyl;

Y is O, S, or —NR$^5$ wherein R$^5$ is hydrogen or benzyl;

R$^3$ is hydrogen, lower alkyl, lower acyl, phenyl, benzoyl, phenyl substituted with lower alkyl, phenyl substituted on the phenyl ring with halogen or methoxy, phenyl substituted with lower alkyl and substituted on the phenyl ring with halogen or methoxy, diphenyl, diphenyl substituted with lower alkyl, diphenyl substituted on each phenyl ring with halogen or methoxy, diphenyl substituted with lower alkyl and substituted on each phenyl ring with halogen or methoxy, triphenyl, triphenyl substituted with lower alkyl, triphenyl substituted on each phenyl ring with halogen or methoxy, triphenyl substituted with lower alkyl and substituted on each phenyl ring with halogen or methoxy, dibenzosulfonyl, lower alkylsulfonyl, p-toluenesulfonyl, t-butyldimethylsilyl, or t-butyldiphenylsilyl;

$R^4$ is lower alkyl, benzyl, benzoyl, or —Z—$NR^6R^7$ wherein Z is a lower alkylene group and $R^6$ and $R^7$ are lower alkyl; and X is hydrogen or a halogen atom;

wherein lower means a straight or branched chain of 1 to 6 carbon atoms.

2. A compound according to claim 1 wherein $R^3$ is selected from the group consisting of hydrogen, lower alkyl, lower acyl, and lower alkylsulfonyl.

3. A compound according to claim 1 wherein Y is O, S or NH.

4. A compound according to claim 1 wherein $R^3$ is hydrogen, benzyl, fluorobenzyl, chlorobenzyl, bromobenzyl, methoxybenzyl, difluorobenzhydryl, trimethoxytrityl, methanesulfonyl, p-toluenesulfonyl, t-butyldimethylsilyl, or t-butyldiphenylsilyl.

5. A compound selected from the group consisting of:

(2R, 3R, 4S, 4aS, 10aR)-2-acetoxymethyl-8-chloro 3,4-diacetoxy-10-methyl-2, 3, 4, 4a, 10, 10a-hexahydropyrano [3, 2-b] [1, 4] benzothiazine, (2R, 3S, 4S, 4aS, 10aR)-10-benzyl-8-chloro -3,4-dihydroxy-2-hydroxymethyl-2, 3, 4, 4a, 10, 10a-hexahydropyrano [3, 2-b] [1, 4] benzothiazine, (2R, 3R, 4S, 4aS, 10aR)-2-acetoxymethyl-10-benzyl -8-chloro-3, 4-diacetoxy-2, 3, 4, 4a, 10, 10a-hexahydropyrano [3, 2-b] [1, 4] benzothiazine, (2R, 3R, 4S, 4aS, 10aR)-2-acetoxymethyl-8-chloro -3, 4-diacetoxy-10-(2-diethylaminoethyl)-2, 3, 4, 4a, 10, 10a-hexahydropyrano [3, 2-b] [1, 4] benzothiazine, (2R, 3R, 4S, 4aS, 10aR)-2-acetoxymethyl-8-chloro -3, 4-diacetoxy-10-(3-dimethylaninopropyl)-2, 3, 4, 4a, 10, 10a-hexahydropyrano [3, 2-b] [1, 4] benzothiazine, (2R, 3R, 4S, 4aS, 10aR)-2-acetoxymethyl-8-chloro -3, 4-diacetoxy-10-(2-diethylaminopropyl)-2, 3, 4, 4a, 10, 10a-hexahydropyrano [3, 2-b] [1, 4] benzothiazine, (2R, 3S, 4S, 4aS, 10aR)-8-chloro-3, 4-dihydroxy-2 -hydroxymethyl-10-methyl-2, 3, 4, 4a, 10, 10a-hexahydropyrano [3, 2-b] [1, 4] benzothiazine, (2R, 3S, 4S, 4aS, 10aR)-8-chloro-10 -(2-diethylaminoethyl)-3, 4-dihydroxy-2-hydroxymethyl-2, 3, 4, 4a, 10, 10a-hexahydropyrano [3, 2-b] [1, 4] benzothiazine, (2R, 3S, 4S, 4aS, 10aR)-8-chloro-10-(3-dimethylaminopropyl) -3, 4-dihydroxy-2-hydroxymethyl-2, 3, 4, 4a, 10, 10a-hexahydropyrano [3, 2-b] [1, 4] benzothiazine, (2R, 3S, 4S, 4aS, 10aR)-8-chloro-10-(2-diethylamino propyl)-3, 4-dihydroxy-2-hydroxymethyl-2, 3, 4, 4a, 10, 10a-hexahydropyrano [3, 2-b] [1, 4] benzothiazine, (2R, 3R, 4S, 4aS, 10aR)-8-chloro-10-(2-diethylamino ethyl)-3, 4-dipropionyloxy-2-propionyloxymethyl-2, 3, 4, 4a, 10, 10a-hexahydropyrano [3, 2-b] [1, 4] benzothiazine, (2R, 3R, 4S, 4aS, 10aR)-8-chloro-10-(2-diethylamino ethyl)-2-butyryloxymethyl-3, 4-dibutylyloxy-2, 3, 4, 4a, 10, 10a-hexahydropyrano [3, 2-b] [1, 4] benzothiazine, (2R, 3R, 4S, 4aS, 10aR)-8-chloro-3, 4-dibenzoyloxy-10 -(2-diethylaminoethyl)-2-benzoyloxymethyl-2, 3, 4, 4a, 10, 10a-hexahydropyrano [3, 2-b] [1, 4] benzothiazine, (2R, 3S, 4S, 4aS, 10aR)-2-tert-butyldimethylsilyloxy methyl-8-chloro-10-(2-diethylaminoethyl)-3,4-dihydroxy -2, 3, 4, 4a, 10, 10a-hexahydropyrano [3, 2-b] [1, 4] benzothiazine, (2R, 3R, 4S, 4aS, 10aR)-2-tert-butyldimethylsilyloxymethyl -8-chloro-3,4-diacetoxy-10-(2-diethylaminoethyl)-2, 3, 4, 4a, 10, 10a-hexahydropyrano [3, 2-b] [1, 4] benzothiazine, (2R, 3R, 4S, 4aS, 10aR)-4-acetoxy-2-acetoxymethyl -8-chloro-10-(2-diethylaminoethyl)-3-hydroxy-2, 3, 4, 4a, 10, 10a-hexahydropyrano [3, 2-b] [1, 4] benzothiazine, (2R, 3S, 4S, 4aS, 10aR)-3-acetoxy-2-acetoxymethyl -3-chloro-10-(2-diethylaminoethyl)-4-hydroxy-2, 3, 4, 4a, 10, 10a-hexahydropyrano [3, 2-b] [1, 4] benzothiazine, (2R, 3S, 4S, 4aS, 10aR)-2-acetoxymethyl-8-chloro -10-(2-diethylaminoethyl)-3, 4-dihydroxy-2, 3, 4, 4a, 10, 10a-hexahydropyrano [3, 2-b] [1, 4] benzothiazine, (2R, 3S, 4S, 4aS, 10aR)-2-tert-butyldimethylsilyloxymethyl -8-chloro-10-(2-diethylaminopropyl)-3,4-dihydroxy -2, 3, 4, 4a, 10, 10a-hexahydropyrano [3, 2-b] [1, 4] benzothiazine, (2R, 3R, 4S, 4aS, 10aR)-2-acetoxymethyl-10-benzoyl-3, 4-diacetoxy-2, 3, 4, 4a, 10, 10a-hexahydropyrano [3, 2-b] [1, 4] benzothiazine, (2R, 3R, 4S, 4aS, 10aR)-2-acetoxymethyl-10-benzyl-3, 4-diacetoxy-2, 3, 4, 4a, 10, 10a-hexahydropyrano [3, 2-b] [1, 4] benzothiazine, (2R, 3S, 4S, 4aS, 10aR)-8-chloro-10-(2-diethylaminoethyl) -3,4-dihydroxy-2-tert-butyldiphenylsilyloxymethyl -2, 3, 4, 4a, 10, 10a-hexahydropyrano [3, 2-b] [1, 4] benzothiazine, (2R, 3R, 4S, 4aS, 10aR)-8-chloro-10-(2-diethylaminoethyl) -3,4-dimethoxymethyloxy-2-hydroxymethyl -2, 3, 4, 4a, 10, 10a-hexahydropyrano [3, 2-b] [1, 4] benzothiazine, (2R, 3R, 4S, 4aS, 10aR)-8-chloro-10-(2-diethylaminoethyl) -3,4-dimethoxymethyloxy-2-methoxymethyl-2, 3, 4, 4a, 10, 10a-hexahydropyrano [3, 2-b] [1, 4] benzothiazine, (2R, 3S, 4S, 4aS, 10aR)-8-chloro-10-(2-diethylaminoethyl) -3,4-dihydroxy-2-methoxymethyl-2, 3, 4, 4a, 10, 10a-hexahydropyrano [3, 2-b] [1, 4] benzothiazine, (2R, 3R, 4S, 4aS, 10aR)-2-benzyloxymethyl-8-chloro -10-(2-diethylaminoethyl)-3,4-dimethoxymethyloxy-2, 3, 4, 4a, 10, 10a-hexahydropyrano [3, 2-b] [1, 4] benzothiazine, (2R, 3S, 4S, 4aS, 10aR)-2-benzyloxymethyl-8-chloro -10-(2-diethylaminoethyl)-3,4-dihydroxy-2, 3, 4, 4a, 10, 10a-hexahydropyrano [3, 2-b] [1, 4] benzothiazine, (2R, 3R, 4S, 4aS, 10aR)-2-benzhydryloxymethyl-8 -chloro-10-(2-diethylaminoethyl)-3,4-dimethoxymethyloxy-2, 3, 4, 4a, 10, 10a-hexahydropyrano [3, 2-b] [1, 4] benzothiazine, (2R, 3S, 4S, 4aS, 10aR)-2-benzhydryloxymethyl-8 -chloro-10-(2-diethylaminoethyl)-3,4-dihydroxy-2, 3, 4, 4a, 10, 10a-hexahydropyrano [3, 2-b] [1, 4] benzothiazine, (2R, 3R, 4S, 4aS, 10aR)-8-chloro-10-(2-diethylaminoethyl) -3, 4-dimethoxymethyloxy-2-(4-fluorobenzyl) oxymethyl -2, 3 4, 4a, 10, 10a-hexahydropyrano [3, 2-b] [1, 4] benzothiazine, (2R, 3S, 4S, 4aS, 10aR)-8-chloro-10-(2-diethylaminoethyl) -3, 4-dihydroxy-2-(4-fluorobenzyl)oxymethyl-2, 3, 4, 4a, 10, 10a-hexahydropyrano [3, 2-b] [1, 4] benzothiazine, (2R, 3S, 4S, 4aS, 10aR)-8-chloro-10-(2-diethylaminoethyl) -3,4-dihydroxy-2-trityloxymethly-2, 3, 4, 4a, 10, 10a-hexahydropyrano [3, 2-hi [1, 4] benzothiazine, (2R, 3S, 4S, 4aS, 10aR)-8-chloro-10-(2-diethylaminoethyl) -3, 4-dihydroxy-2-[tris (4-methoxyphenyl) methyloxymethyl]-2, 3, 4, 4a, 10, 10a-hexahydropyrano [3, 2-b] 1, 4] benzothiazine, (2R, 3R, 4S, 4aS, 10aR)-8-chloro-3, 4-diacetoxy-10 -2-diethylaminoethyl)-2-(4-methylphenylsulfonyloxy)-2, 3, 4, 10 4a, 10, 10a-hexahydropyrano [3, 2-b] [1, 4] benzothiazine, (2R, 3S, 4S, 4aS, 10aR)-2-benzylaminomethyl -8-chloro-10-(2-diethylaminoethyl)-3, 4-dihydroxy-2, 3, 4, 4a, 10, 10a -hexahydropyrano [3, 2-b] [1, 4] benzothiazine, (2R, 3S, 4S, 4aS, 10aR)-2-benzhydrylaminomethyl -8-chloro-10-(2-diethylaminoethyl)-3, 4-dihydroxy-2, 3, 4, 4a, 10, 10a-hexahydropyrano ]3, 2-b] [1, 4] benzothiazine, (2R, 3S, 4S, 4aS, 10aR)-8-chloro-10 -(2-diethylaminoethyl)-3, 4-dihydroxy-2-tritylaminomethyl-2, 3, 4, 4a, 10, 10a-hexahydropyrano [3, 2-b] [1, 4] benzothiazine, (2R, 3S, 4S, 4aS, 10aR)-8-chloro-2-dibenzylaminomethyl -10-(2-diethylaminoethyl)-3, 4-dihydroxy-2, 3, 4, 4a, 10, 10a-hexahydropyrano [3, 2-b] [1, 4] benzothiazine, (2R, 3S, 4S, 4aS, 10aR)-8-chloro-10-(2-diethylaminoethyl) -2-[(10, 11-dihydro-5H-dibenzo [a, d] cycloheptene -5-yl)aminomethyl]-3, 4-dihydroxy-2, 3, 4, 4a, 10, 10a-hexahydropyrano [3, 2-b] [1, 4] benzothiazine, (2R, 3R, 4S, 4aS, 10aR)-2-acetylthio-8-chloro -3, 4-diacetoxy-10-(2-diethylaminoethyl)-2, 3, 4, 4a, 10, 10a-hexahydropyrano [3, 2-b] [1, 4] benzothiazine, (2R, 3S, 4S, 4aS, 10aR)-8-chloro-10 -(2-diethylaminoethyl)-3, 4-dihydroxy-2-mercaptomethyl-2, 3, 4, 4a, 10, 10a-hexahydropyrano [3, 2-b] [1, 4] benzothiazine, (2S, 3S, 4S, 4aS, 10aR)-8-chloro-10-(2-diethylaminoethyl) -3, 4-dihydroxy-2-methylthiomethyl-2, 3, 4, 4a, 10, 10a-hexahydropyrano [3, 2-b] [1, 4] benzothiazine, (2S, 3S, 4S, 4aS, 10aR)-2-benzylthiomethyl-8-chloro -10-(2-diethylaminoethyl)-3, 4-dihydroxy-2, 3, 4, 4a, 10, 10a-hexahydropyrano [3, 2-b] [1, 4] benzothiazine, (2S 3S 4S 4aS 10aR) 2-benzhydrylthiomethyl-8 -chloro-10-(2-diethylaminoethyl)-3, 4-dihydroxy-2, 3, 4, 4a, 10, 10a-hexahydropyrano [3, 2-b] [1, 4] benzothiazine, (2S, 3S, 4S, 4aS, 10aR)-8-chloro-10-(2-diethylaminoethyl) -3, 4-dihydroxy-2-tritylthiomethyl-2, 3, 4, 4a, 10, 10a-hexahydropyrano [3, 2-b ] [1, 4] benzothiazine, (2S, 3S, 4S, 4aS, 10aR)-8-chloro-10-(2-diethylaminoethyl) -3, 4-dihydroxy-2-phenetylthiomethyl-2, 3, 4, 4a, 10, 10a-hexahydropyrano [3, 2-b] [1, 4] benzothiazine, (2S, 3S, 4S, 4aS, 10aR)-8-chloro-10-(2-diethylaminoethyl) -3, 4-dihydroxy-2-(4-fluorobenzylthiomethyl)-2, 3, 4, 4a, 10, 10a-hexahydropyrano [3, 2-b] [1, 4] benzothiazine, (2S, 3S, 4S, 4aS, 10aR)-8-chloro-10-(2-diethylaminoethyl) -3, 4-dihydroxy-2-phenylthiomethyl-2, 3, 4, 4a, 10, 10a-hexahydropyrano [3, 2-b] [1, 4] benzothiazine, and (2S, 3S, 4S, 4aS, 10aR)-8-chloro-10-(2-dlethylaminoethyl) -3, 4-dihydroxy-2-trityloxymethyl-2, 3, 4, 4a, 10, 10a-hexahydropyrano [3, 2-b] [1, 4] benzothiazine hydrochloride hemihydrate.

6. A pharmaceutical composition for activating brain metabolism comprising an effective amount of a compound according to claim 1 and an inert carrier.

7. A pharmaceutical composition for improving cerebral function comprising an effective amount of a compound according to claim 1 and an inert carrier.

8. A hexahydropyrano [3,2-b] [1,4] benzothiazine compound selected from the group consisting of:

(6aR, 7aR, 13aS, 14S, 14aR)-10-chloro-8 -(2-diethylaminoethyl)-14-hydroxy-2,2,4,4-tetraisopropyl-6H-6a, 7a, 8, 13a, 14, 14a-hexahydro [1,3,5,2,4] trioxadisiloxyno [6', 7': 5, 6] pyrano [3,2-b] [1,4] benzothiazine;

(6aR, 7aR, 13aS, 14S, 14aR)-14-acetoxyl-10-chloro-8 -(2-diethylaminoethyl)-2,2,4,4-tetraisopropyl-6H-6a, 7a, 8, 13a, 14, 14a-hexahydro [1,3,5,2,4] trioxadisiloxyno [6', 7': 5,6] pyrano [3,2-b] [1,4] benzothiazine;

(2R, 3R, 4aS, 10aR)-2-azidomethyl-8-chloro -3,4-diacetoxy-10-(2-diethylaminoethyl)-2,3,4,4a, 10, 10a-hexahydropyrano [3,2-b] [1,4] benzothiazine;

(2R, 3S, 4S, 4aS, 10aR)-2-azidomethyl-8-chloro-10 -(2-diethylaminoethyl)-3,4-dihydroxy-2,3,4,4a, 10, 10a-hexahydropyrano [3,2-b] [1,4] benzothiazine;

(2R, 3R, 4S, 4aS, 10aR)-2-azidomethyl-8-chloro-10 -(2-diethylaminoethyl)-3,4-(1,1,3,3-tetraisopropyldisiloxane -1,3-diyldioxy)-2,3,4,4a, 10, 10a-hexahydropyrano [3,2-b] [1,4] benzothiazine;

(2R, 3R, 4S, 4aS, 10aR)-2-aminomethyl-8-chloro-10 -(2-diethylaminoethyl)-3,4-(1,1,3,3-tetraisopropyldisiloxane -1,3-diyldioxy)-2,3,4,4a, 10, 10a-hexahydropyrano [3,2-b] [1,4] benzothiazine;

(2R, 3R, 4S, 4aS, 10aR)-2-benzylaminomethyl-8-chloro -10-(2-diethylaminoethyl)-3,4-(1,1,3,3-tetraisopropyl-disiloxane -1,3-diyldioxy)-2,3,4,4a, 10, 10a-hexahydropyrano [3,2-b] [1,4] benzothiazine;

(2R, 3R, 4S, 4aS, 10aR)-2-benzhydrylaminomethyl-8-chloro -10-(2-diethylaminoethyl)-3,4-(1,1,3,3 -tetraisopropyldisiloxane-1,3-diyldioxy)-2,3,4,4a, 10, 10a-hexahydropyrano [3,2-b] [1,4] benzothiazine;

(2R, 3R, 4S, 4aS, 10aR)-8-chloro-10 -(2diethylaminoethyl)-3,4-(1,1,3,3-tetraisopropyldisiloxane-1,3-diyldioxy) -2-tritylaminomethyl-2,3,4,4a, 10, 10a-hexahydropyrano [3,2-b] [1,4] benzothiazine;

(2R, 3R, 4S, 4aS, 10aR)-8-chloro -2-dibenzylaminomethyl-10-(2-diethylaminoethyl)-3,4-(1,1,3,3 -tetraisopropyldisiloxane-1,3-diyldioxy)-2,3,4,4a, 10, 10a-hexahydropyrano [3,2-b] [1,4] benzothiazine;

(2R, 3R, 4S, 4aS, 10aR)-8-chloro-10 -(2-diethylaminoethyl)-2-[(10, 11-dihydro-5H-dibenzo [a,d] cycloheptene-5-yl)aminomethyl]-3,4 -(1,1,3,3-tetraisopropyldisiloxane-1,3-diyldioxy)-2,3,4,4a, 10, 10a-hexahydropyrano [3,2-b] [1,4] benzothiazine; and pharmaceutically acceptable acid-addition salts thereof.

9. A pharmaceutical composition for activating brain metabolism comprising an effective amount of a compound according to claim 8 and a pharmaceutically acceptable carrier.

10. A pharmaceutical composition for improving cerebral function comprising an effective amount of a compound according to claim 8 and a pharmaceutically acceptable carrier.

* * * * *